(12) United States Patent
Dorwald et al.

(10) Patent No.: US 6,673,829 B2
(45) Date of Patent: Jan. 6, 2004

(54) AMINOAZETIDINE,-PYRROLIDINE AND -PIPERIDINE DERIVATIVES

(75) Inventors: Florencio Zaragoza Dorwald, Ballerup (DK); Rolf Hohlweg, Kvistgaard (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 10/242,968

(22) Filed: Sep. 12, 2002

(65) Prior Publication Data

US 2003/0130253 A1 Jul. 10, 2003

Related U.S. Application Data

(60) Provisional application No. 60/383,418, filed on May 21, 2002.

(30) Foreign Application Priority Data

Sep. 14, 2001 (DK) .................................. 2001-01344
May 21, 2002 (DK) .................................. 2002 00750

(51) Int. Cl.$^7$ ...................... A61K 31/40; C07D 207/14
(52) U.S. Cl. ...................... 514/426; 548/557; 548/526; 548/953; 546/207; 546/224; 514/210; 514/321; 514/329; 514/422
(58) Field of Search ...................... 514/426, 422, 514/329, 321, 210; 548/557, 526, 953; 546/224, 207

(56) References Cited

U.S. PATENT DOCUMENTS

| | | | | |
|---|---|---|---|---|
| 3,787,419 | A | | 1/1974 | Bruce .................... 260/293.77 |
| 3,963,745 | A | | 6/1976 | Cale, Jr. et al. ......... 260/326.5 |
| 3,966,957 | A | * | 6/1976 | Cale et al. .................... 424/274 |
| 4,002,757 | A | | 1/1977 | Cale, Jr. ..................... 424/258 |
| 4,039,678 | A | * | 8/1977 | Cale ............................ 424/274 |
| 4,049,821 | A | * | 9/1977 | Funderburk ................ 424/274 |
| 4,109,005 | A | | 8/1978 | Lunsford et al. ........... 424/274 |
| 5,571,832 | A | | 11/1996 | De Costa et al. ........... 514/408 |
| 6,090,802 | A | | 7/2000 | Kawamoto et al. ......... 514/210 |
| 6,316,475 | B1 | | 11/2001 | Bennani et al. ............. 514/343 |

FOREIGN PATENT DOCUMENTS

| | | |
|---|---|---|
| BE | 861 790 | 3/1978 |
| DE | 1 964 516 | 7/1970 |
| DE | 24 61 802 | 7/1975 |
| DE | 25 58 348 | 7/1976 |
| EP | 0518558 A1 | 6/1992 |
| EP | 0978512 A1 | 7/1998 |
| GB | 1088531 | 10/1967 |
| GB | 1364231 | 8/1974 |
| JP | 07-48375 | 2/1996 |
| NL | 6500326 | 1/1968 |
| WO | WO 96/29307 | 9/1996 |
| WO | WO 97/09308 | 3/1997 |
| WO | WO 97/17345 | 5/1997 |
| WO | WO 97/23483 | 7/1997 |
| WO | WO 99/42458 | 8/1999 |
| WO | WO 02/22592 A2 A3 | 3/2001 |
| WO | WO 01/44191 A1 | 6/2001 |
| WO | WO 01/66534 A2 | 9/2001 |
| WO | WO 01/74773 A2 | 10/2001 |
| WO | WO 01/74810 A2 | 10/2001 |
| WO | WO 01/74813 A2 | 10/2001 |
| WO | WO 01/74814 A1 | 10/2001 |
| WO | WO 02/06223 A1 | 1/2002 |
| WO | WO 02/012190 A2 A3 | 2/2002 |
| WO | WO 02/49648 A1 | 6/2002 |
| WO | WO 01/74815 A2 | 10/2002 |

OTHER PUBLICATIONS de Costa, J. Med. Chem. vol. 35, pp. 4334–4343 (1992).
Dostert et al., Eur. J. Med. Chem.—Chim. Ther., vol. 17 No. 5, pp. 437–444 (1982).
Fouchard et al., Arzneim.-Forsch./Drug Res. vol. 49, No. I, pp. 96–105 (1999).
Ganellin et al., Arch. Pharm. Pharm. Med. Chem., vol. 331, pp. 395–404 (1998).
Gravbiel et al., Aviation, Space, and Environmental Medicine, pp. 867–871 (1977).
Irikura, Yakugaku Zasshi, vol. 82, pp. 356–363 (1962) (English abstract).
Jacobson et al., NIDA Res. Monogr., vol. 1, pp. 179–195 (1993).
Linney et al., Journal of Medicinal Chemistry, vol. 43, No. 12, pp. 2363–2370 (2000).
Lovenberg et al., Molecular Pharmacology, vol. 55, pp. 1101–1107 (1999).
Meltzer et al., Acta Pharm Suec. Suppl. 1, pp. 200–218 (1983).
Meltzer et al. Life Sciences, vol. 32, pp. 2877–2886 (1983).
Morisset et al., Nature, vol. 408, pp. 860–864 (2000).
Narcisse et al., Therapie, vol. 32, pp. 121–132 (1977).
Ohkubo et al., Chem. Pharm. Bull. vol. 43, No. 6, pp. 947–954 (1995).
Singh et al., Progress in Drug Research, vol. 45, pp. 108–165.
Stark et al., Drugs of the Future, vol. 21, No. 5, pp. 507–520 (1996).
Tozer et al., Exp. Opin. Ther. Patents, vol. 10, No. 7, pp. 1045–1055 (2000).
Walczynski et al., Arch. Pharm. Pharm. Med. Chem., vol. 332, pp. 389–398.
Walczynski et al., Elsevier, Il Farmaco, vol. 54, pp. 684–694 (1999).

* cited by examiner

Primary Examiner—Charanjit S. Aulakh
(74) Attorney, Agent, or Firm—Cheryl Agris, Esq.; Richard Bork, Esq.; Reza Green, Esq.

(57) ABSTRACT

Novel aminoazetidine, -pyrrolidine, and -piperidine derivatives, use of these compounds as pharmaceutical compositions, pharmaceutical compositions comprising the compounds, and a method of treatment employing these compounds and compositions. The compounds show a high and selective binding affinity to the histamine H3 receptor indicating histamine H3 receptor antagonistic, inverse agonistic or agonistic activity. As a result, the compounds are useful for the treatment of diseases and disorders related to the histamine H3 receptor.

28 Claims, No Drawings

AMINOAZETIDINE,-PYRROLIDINE AND -PIPERIDINE DERIVATIVES

PRIORITY CLAIM

This application claims priority under 35 U.S.C. 119 of Danish application no. PA 2002 00750 filed May 16, 2002, Danish application no. PA 2001 01344 filed Sep. 14, 2001 and U.S. provisional application No. 60/383,418 filed May 21, 2002, the contents of which are fully incorporated herein by reference.

FIELD OF THE INVENTION

The present invention relates to novel aminoazetidine, -pyrrolidine and -piperidine derivatives, to the use of these compounds as pharmaceutical compositions, to pharmaceutical compositions comprising the compounds, and to a method of treatment employing these compounds and compositions. The present compounds show a high and selective binding affinity to the histamine H3 receptor indicating histamine H3 receptor antagonistic, inverse agonistic or agonistic activity. As a result, the compounds are useful for the treatment of diseases and disorders related to the histamine H3 receptor.

BACKGROUND OF THE INVENTION

The existence of the histamine H3 receptor has been known for several years and the receptor is of current interest for the development of new medicaments (see eg Stark et al., Drugs Fut. 1996, 21, 507–520; Leurs et al., Progress in Drug Research 1995, 45, 107–165). Recently, the human histamine H3 receptor has been cloned, cf Lovenberg et al, Molecular Pharmacology, June 1999, 55, 1101–1107. The histamine H3 receptor is a presynaptic autoreceptor located both in the central and the peripheral nervous system, the skin and in organs such as the lung, the intestine, probably the spleen and the gastrointestinal tract. Recent evidence suggests that the H3 receptor shows intrinsic, constitutive activity, in vitro as well as in vivo (ie it is active in the absence of an agonist; see eg Morisset et al., Nature 2000, 408, 860–864). Compounds acting as inverse agonists can inhibit this activity. The histamine H3 receptor has been demonstrated to regulate the release of histamine and also of other neurotransmitters such as serotonin and acetylcholine. A histamine H3 receptor antagonist or inverse agonist would therefore be expected to increase the release of these neurotransmitters in the brain. A histamine H3 receptor agonist, on the contrary, leads to an inhibition of the biosynthesis of histamine and an inhibition of the release of histamine and also of other neurotransmitters such as serotonin and acetylcholine. These findings suggest that histamine H3 receptor agonists, inverse agonists and antagonists could be important mediators of neuronal activity. Accordingly, the histamine H3 receptor is an important target for new therapeutics.

Compounds similar to the compounds of the present invention have previously been disclosed, cf U.S. Pat. No. 3,963,745, U.S. Pat. No. 3,966,957, DE 25 58 348, U.S. Pat. No. 6,090,802, WO 97/23483, WO 97/09308, JP 07048375, EP 518 558, Acta Pharm Suec. Suppl. 1, 200–218, 1983, Life Sci., 32(25), 2877–2886, 1983, U.S. Pat. No. 4,109,005, BE 861790, Aviat. Space Environ. Med., 48(9), 867–871, 1977, U.S. Pat. No. 4,049,821, U.S. Pat. No. 4,039,678, Therapie 1977, 32(1), 121–132, U.S. Pat. No. 4,002,757 DE 19 64 516, NL 6500326, U.S. Pat. No. 3,787,419, Irikura, Yakugaku Zasshi 1962, 82, 356, DE 24 61 802, Eur. J. Chem. Chim. Ther. 1982, 17, 437, J. Med. Chem. 1992, 35, 4334, Chem. Pharm. Bull. 1995, 43, 947, Arzneim. Forsch. 1999, 49, 96, U.S. Pat. No. 5,571,832, NIDA Res. Monogr. 1993, 140 (Problems of Drug Dependence, volume 1), 179–195. However, these references neither disclose nor suggest that these compounds may have a histamine H3 receptor antagonistic or agonistic activity.

Several publications disclose the preparation and use of histamine H3 agonists and antagonists. Most of these are imidazole derivatives (see eg Stark et al., Drugs of the Future 1996, 21, 507–520; Tozer, Kalinddjian, Expert Opinion on Therapeutic Patents 2000, 10, 1045–1055). However, recently some imidazole-free ligands of the histamine H3 receptor have been described (see eg Walczynski et al., Arch. Pharm. Pharm. Med. Chem. 1999, 332, 389–398; Linney et al., J. Med. Chem. 2000, 43, 2362–2370; Ganellin et al., Arch. Pharm. Pharm. Med. Chem. 1998, 331, 395–404; Walczynski et al., Il Farmaco 1999, 54, 684–694; WO 99/42458, EP 0 978 512, WO 97/17345, U.S. Pat. No. 6,316,475, WO 01/66534, WO 01/74810, WO 01/44191, WO 01/74815, WO 01/74773, WO 01/74813, WO 01/74814 and WO 02/12190.

However, these compounds differ structurally from the present compounds.

In view of the art's interest in histamine H3 receptor agonists, inverse agonists and antagonists, novel compounds which interact with the histamine H3 receptor would be a highly desirable contribution to the art. The present invention provides such a contribution to the art being based on the finding that a novel class of aminoazetidine, -pyrrolidine and -piperidine derivatives has a high and specific affinity to and potency at the histamine H3 receptor.

Due to their interaction with the histamine H3 receptor, the present compounds are useful in the treatment of a wide range of conditions and disorders in which an interaction with the histamine H3 receptor is beneficial. Thus, the compounds may find use eg in the treatment of diseases of the central nervous system, the peripheral nervous system, the cardiovascular system, the pulmonary system, the gastrointestinal system and the endocrinological system.

SUMMARY OF THE INVENTION

The invention relates to a compound of the general formula (I):

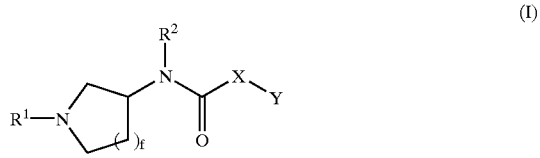

wherein
R$^1$ represents
  hydrogen,
  $C_{1-8}$-alkyl, $C_{3-8}$-alkenyl or $C_{3-8}$-alkynyl, which may optionally be substituted with one or more halogen atoms,
  $C_{3-7}$-cycloalkyl, $C_{3-7}$-cycloalkenyl, $C_{4-8}$-bicycloalkyl, $C_{3-7}$-cycloalkyl-$C_{1-3}$-alkyl or $C_{3-7}$-cycloalkenyl-$C_{1-3}$-alkyl, which may optionally be substituted at any position with one or more halogen-atoms,
R$^2$ represents $C_{1-6}$-alkyl,
f is 0, 1 or 2,
X represents —(CH$_2$)$_m$—(Z)$_n$—(CH$_2$)$_o$—,
m and o independently are 0, 1, 2, 3 or 4, n is 0 or 1, Z is —O—, —NH—, —N(CH$_3$)—, —C(=O)—, —CH(OH)—, —CH(O—C$_{1-6}$-alkyl)-, —C(=N—OH)—, —S—, —S(=O)—, —S(=O)$_2$—, —CH=CH— or —C≡C—, Y is (a) aryl or heteroaryl, which may optionally be substituted with one or more substituents selected from halogen, nitro, cyano, hydroxy, C$_{1-6}$-alkanoyl, C$_{1-6}$-alkylthio, C$_{1-6}$-alkylsulfonyl, C$_{1-6}$-alkyl, C$_{1-6}$-alkoxy, C$_{3-8}$-cycloalkyl, trifluoromethyl, trifluoromethoxy, —NR$^3$R$^4$ and —O(C=O)NR$^3$R$^4$, or wherein two substituents in adjacent positions form a radical —O—(CH$_2$)$_{1-3}$—O—, wherein R$^3$ and R$^4$ independently are hydrogen, C$_{1-6}$-alkyl, C$_{3-8}$-cycloalkyl, C$_{1-6}$-alkanoyl or aryl, or R$^3$ and R$^4$ together with the nitrogen atom to which they are attached form a 4 to 7 membered, saturated or unsaturated azetidinyl, pyrrolidinyl, piperidyl or azepanyl ring, aryl, aryloxy, aryl-C$_{1-6}$-alkyl and aryl-C$_{1-6}$-alkoxy, wherein the ring moieties optionally may be substituted with one or more substituents selected from halogen, nitro, cyano, hydroxy, C$_{1-6}$-alkanoyl, C$_{1-6}$-alkylthio, C$_{1-6}$-alkylsulfonyl, C$_{1-6}$-alkyl, C$_{1-6}$-alkoxy, C$_{3-8}$-cycloalkyl, trifluoromethyl, trifluoromethoxy, —NR$^5$R$^6$ and —O(C=O)NR$^5$R$^6$, or wherein two substituents in adjacent positions form a radical —O—(CH$_2$)$_{1-3}$—O—, wherein R$^5$ and R$^6$ independently are hydrogen, C$_{1-6}$-alkyl, C$_{3-8}$-cycloalkyl, C$_{1-6}$-alkanoyl or aryl, or R$^5$ and R$^6$ together with the nitrogen atom to which they are attached form a 4 to 7 membered, saturated or unsaturated azetidinyl, pyrrolidinyl, piperidyl or azepanyl ring, (b) C$_{3-8}$-cycloalkyl or C$_{5-8}$-cycloalkenyl, which may optionally be substituted with one or more substituents selected from C$_{1-6}$-alkyl, C$_{1-6}$-alkoxy, C$_{1-6}$-alkylthio, cyano, trifluoromethyl, trifluoromethoxy and halogen, aryl and aryloxy, wherein the ring moieties optionally may be substituted with one or more substituents selected from halogen, nitro, cyano, hydroxy, C$_{1-6}$-alkanoyl, C$_{1-6}$-alkylthio, C$_{1-6}$-alkylsulfonyl, C$_{1-6}$-alkyl, C$_{1-6}$-alkoxy, C$_{3-8}$-cycloalkyl, trifluoromethyl, trifluoromethoxy, —NR$^7$R$^8$ and —O(C=O)NR$^7$R$^8$, or wherein two substituents in adjacent positions form a radical —O—(CH$_2$)$_{1-3}$—O—, wherein R$^7$ and R$^8$ independently are hydrogen, C$_{1-6}$-alkyl, C$_{3-8}$-cycloalkyl, C$_{1-6}$-alkanoyl or aryl, or R$^7$ and R$^8$ together with the nitrogen atom to which they are attached form a 4 to 7 membered, saturated or unsaturated azetidinyl, pyrrolidinyl, piperidyl or azepanyl ring, as well as any diastereomer or enantiomer or tautomeric form thereof including mixtures of these or a pharmaceutically acceptable salt thereof, with the proviso that, when m, n, and o are 0, R$^1$ must not be cyclopentyl, cyclohexyl, ethyl, or methyl, and with the proviso that the compound must not be

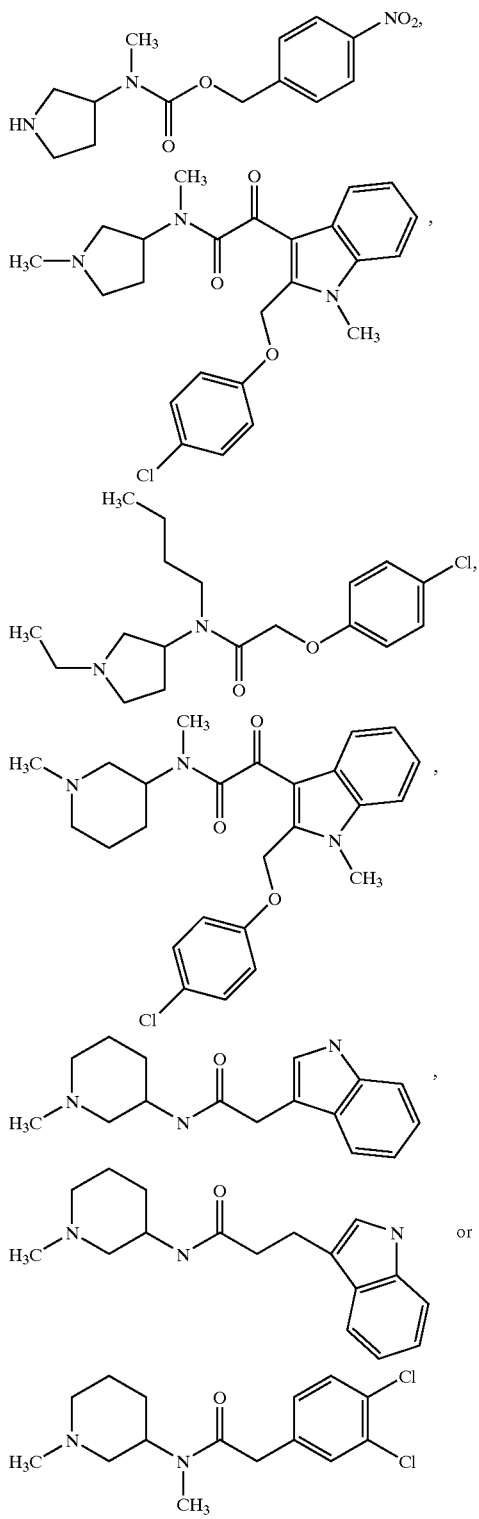

Definitions

In the structural formulae given herein and throughout the present specification, the following terms have the indicated meaning:

The term "halogen" means F, Cl, Br or I.

The term "C$_{1-6}$-alkyl" as used herein represents a saturated, branched or straight hydrocarbon group having from 1 to 6 carbon atoms. Typical $C_{1-6}$-alkyl groups include, but are not limited to, methyl, ethyl, n-propyl, isopropyl, butyl, isobutyl, sec-butyl, tert-butyl, pentyl, hexyl and the like.

In the same way the terms "$C_{1-3}$-alkyl" and "$C_{1-8}$-alkyl" as used herein represent saturated, branched or straight hydrocarbon groups having from 1 to 3 carbon atoms and from 1 to 8 carbon atoms, respectively.

The term "$C_{3-8}$-alkenyl" as used herein represents a branched or straight hydrocarbon group having from 3 to 8 carbon atoms and at least one double bond. Typical $C_{3-8}$-alkenyl groups include, but are not limited to, 1-propenyl, 2-propenyl, isopropenyl, 1,3-butadienyl, 1-butenyl, 2-butenyl, 1-pentenyl, 2-pentenyl, 1-hexenyl, 2-hexenyl, 2-heptenyl, 2-octenyl, 1-ethylprop-2-enyl, 1,1-(dimethyl)prop-2-enyl, 1-ethylbut-3-enyl, 1,1-(dimethyl)but-2-enyl, 1,1-(dimethyl)pent-3-enyl, 1-ethylpent-2-enyl, 1,1-(dimethyl)pent-3-enyl, 1,1-(dimethyl)hex-3-enyl, 1-ethylhex-4-enyl and the like.

The term "$C_{3-8}$-alkynyl" as used herein represents a branched or straight hydrocarbon group having from 3 to 8 carbon atoms and at least one triple bond. Typical $C_{3-8}$-alkynyl groups include, but are not limited to, 1-propynyl, 2-propynyl, isopropynyl, 1,3-butadiynyl, 1-butynyl, 2-butynyl, 1-pentynyl, 2-pentynyl, 1-hexynyl, 2-hexynyl, 2-heptynyl, 2-octynyl, 1-ethylprop-2-ynyl, 1,1-(dimethyl)prop-2-ynyl, 1-ethylbut-3-ynyl, 1,1-(dimethyl)but-2-ynyl, 1,1-(dimethyl)pent-3-ynyl, 1-ethylpent-2-ynyl, 1,1-(dimethyl)pent-3-ynyl, 1,1-(dimethyl)hex-3-ynyl, 1-ethylhex-4-ynyl and the like.

The term "$C_{1-6}$-alkoxy" as used herein refers to the radical —O—$C_{1-6}$-alkyl, wherein $C_{1-6}$-alkyl is as defined above. Representative examples are methoxy, ethoxy, n-propoxy, isopropoxy, butoxy, sec-butoxy, tert-butoxy, pentoxy, isopentoxy, hexoxy, isohexoxy and the like.

The term "$C_{1-6}$-alkanoyl" as used herein refers to the radical —C(=O)H or —C(=O)$C_{1-5}$-alkyl, wherein $C_{1-5}$-alkyl represents a saturated, branched or straight hydrocarbon groups having from 1 to 5 carbon atoms. Representative examples are acetyl, propionyl, butanoyl, pentanoyl, hexanoyl, and the like.

The term "$C_{1-6}$-alkylthio as used herein refers to the radical —S—$C_{1-6}$-alkyl, wherein $C_{1-6}$-alkyl represents a saturated, branched or straight hydrocarbon groups having from 1 to 6 carbon atoms as defined above. Representative examples are methylthio, ethylthio, propylthio, butylthio, pentylthio, hexylthio, and the like The term "$C_{1-6}$-alkylsulfonyl" as used herein refers to the radical —S(=O)$_2$—$C_{1-6}$-alkyl, wherein $C_{1-6}$-alkyl represents a saturated, branched or straight hydrocarbon groups having from 1 to 6 carbon atoms as defined above. Representative examples are methylsulfonyl, ethylsulfonyl, propylsulfonyl, butylsulfonyl, pentylsulfonyl, hexylsulfonyl, and the like.

The term "$C_{3-7}$-cycloalkyl" as used herein represents a saturated, monocyclic, carbocyclic group having from 3 to 7 carbon atoms. Representative examples are cyclopropyl, cyclobutyl, cyclopentyl, cyclohexyl, cycloheptyl and the like.

The term "$C_{3-7}$-cycloalkenyl" as used herein represents a monocyclic, carbocyclic, non-aromatic group having from 3 to 7 carbon atoms and at least one double bond. Representative examples are cyclopropenyl, cyclobutenyl, cyclopentenyl and the like.

In the same way the term "$C_{5-8}$-cycloalkenyl" as used herein represent a monocyclic, carbocyclic, non-aromatic group having from 5 to 8 carbon atoms and at least one double bond.

The term "$C_{4-8}$-bicycloalkyl" as used herein represents a saturated, bicyclic, carbocyclic group having from 4 to 8 carbon atoms. Representative examples are bicyclo-[3.1.0]hexyl, bicyclo[4.1.0]heptyl, bicyclo[3.1.1]heptyl, bicyclo[2.2.1]heptyl and the like.

The term "aryl" as used herein is intended to include carbocyclic aromatic ring systems such as phenyl, biphenylyl, naphthyl, anthracenyl, phenanthrenyl, fluorenyl, indenyl, pentalenyl, azulenyl and the like. Aryl is also intended to include the partially hydrogenated derivatives of the carbocyclic systems enumerated above. Non-limiting examples of such partially hydrogenated derivatives are 1,2,3,4-tetrahydronaphthyl, 1,4-dihydronaphthyl and the like.

The term "aryloxy" as used herein refers to the radical —O-aryl, wherein aryl is as defined above. Non-limiting examples are phenoxy, naphthoxy, anthracenyloxy, phenantrenyloxy, fluorenyloxy, indenyloxy and the like.

The term "heteroaryl" as used herein is intended to include heterocyclic aromatic ring systems containing one or more heteroatoms selected from nitrogen, oxygen and sulfur such as furyl, thienyl, pyrrolyl, oxazolyl, thiazolyl, imidazolyl, isoxazolyl, isothiazolyl, 1,2,3-triazolyl, 1,2,4-triazolyl, pyranyl, pyridyl, pyridazinyl, pyrimidinyl, pyrazinyl, 1,2,3-triazinyl, 1,2,4-triazinyl, 1,3,5-triazinyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, tetrazolyl, thiadiazinyl, indolyl, isoindolyl, benzofuryl, benzothienyl, indazolyl, benzimidazolyl, benzothiazolyl, benzoisothiazolyl, benzoxazolyl, benzisoxazolyl, purinyl, quinazolinyl, quinolizinyl, quinolinyl, isoquinolinyl, quinoxalinyl, naphthyridinyl, pteridinyl, carbazolyl, azepinyl, diazepinyl, acridinyl and the like. Heteroaryl is also intended to include the partially hydrogenated derivatives of the heterocyclic systems enumerated above. Non-limiting examples of such partially hydrogenated derivatives are 2,3-dihydrobenzofuranyl, pyrrolinyl, pyrazolinyl, indanyl, indolinyl, oxazolidinyl, oxazolinyl, oxazepinyl and the like.

Certain of the above defined terms may occur more than once in the structural formulae, and upon such occurrence each term shall be defined independently of the other.

"Aryl-$C_{1-6}$-alkyl", "aryl-$C_{1-6}$-alkoxy" etc. mean $C_{1-6}$-alkyl or $C_{1-6}$-alkoxy as defined above, substituted by aryl as defined above, for example:

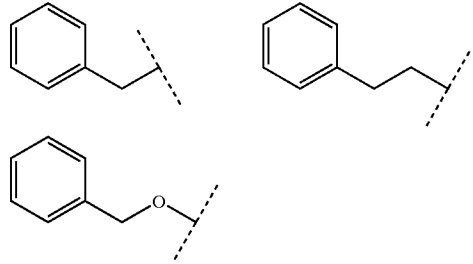

The term "optionally substituted" as used herein means that the groups in question are either unsubstituted or substituted with one or more of the substituents specified. When the groups in question are substituted with more than one substituent the substituents may be the same or different.

The term "treatment" as used herein means the management and care of a patient for the purpose of combating a disease, disorder or condition. The term is intended to include the delaying of the progression of the disease, disorder or condition, the alleviation or relief of symptoms and complications, and/or the cure or elimination of the disease, disorder or condition. The patient to be treated is preferably a mammal, in particular a human being.

DETAILED DESCRIPTION OF THE INVENTION

In one embodiment, Y is
(a) aryl or heteroaryl, which may optionally be substituted with one or more substituents selected from
halogen, nitro, cyano, hydroxy, $C_{1-6}$-alkanoyl, $C_{1-6}$-alkylthio, $C_{1-6}$-alkylsulfonyl, $C_{1-6}$-alkyl, $C_{1-6}$-alkoxy, $C_{3-8}$-cycloalkyl, trifluoromethyl, trifluoromethoxy, —$NR^3R^4$ and —$O(C=O)NR^3R^4$, or wherein two substituents in adjacent positions form a radical —O—$(CH_2)_{1-3}$—O—,
wherein $R^3$ and $R^4$ independently are hydrogen, $C_{1-6}$-alkyl, $C_{3-8}$-cycloalkyl, $C_{1-6}$-alkanoyl or aryl, or $R^3$ and $R^4$ together with the nitrogen atom to which they are attached form a 4 to 7 membered, saturated or unsaturated azetidinyl, pyrrolidinyl, piperidyl or azepanyl ring,
aryl, aryl-$C_{1-6}$-alkyl and aryl-$C_{1-6}$-alkoxy, wherein the ring moieties optionally may be substituted with one or more substituents selected from
halogen, nitro, cyano, hydroxy, $C_{1-6}$-alkanoyl, $C_{1-6}$-alkylthio, $C_{1-6}$-alkylsulfonyl, $C_{1-6}$-alkyl, $C_{1-6}$-alkoxy, $C_{3-8}$-cycloalkyl, trifluoromethyl, trifluoromethoxy, —$NR^5R^6$ and —$O(C=O)NR^5R^6$, or wherein two substituents in adjacent positions form a radical —O—$(CH_2)_{1-3}$—O—,
wherein $R^5$ and $R^6$ independently are hydrogen, $C_{1-6}$-alkyl, $C_{3-8}$-cycloalkyl, $C_{1-6}$-alkanoyl or aryl, or $R^5$ and $R^6$ together with the nitrogen atom to which they are attached form a 4 to 7 membered, saturated or unsaturated azetidinyl, pyrrolidinyl, piperidyl or azepanyl ring,
(b) $C_{3-8}$-cycloalkyl or $C_{5-8}$-cycloalkenyl, which may optionally be substituted with one or more substituents selected from
$C_{1-6}$-alkyl, $C_{1-6}$-alkoxy, $C_{1-6}$-alkylthio, cyano, trifluoromethyl, trifluoromethoxy and halogen,
aryl and aryloxy, wherein the ring moieties optionally may be substituted with one or more substituents selected from
halogen, nitro, cyano, hydroxy, $C_{1-6}$-alkanoyl, $C_{1-6}$-alkylthio, $C_{1-6}$-alkylsulfonyl, $C_{1-6}$-alkyl, $C_{1-6}$-alkoxy, $C_{3-8}$-cycloalkyl, trifluoromethyl, trifluoromethoxy, —$NR^7R^8$ and —$O(C=O)NR^7R^8$, or wherein two substituents in adjacent positions form a radical —O—$(CH_2)_{1-3}$—O—,
wherein $R^7$ and $R^8$ independently are hydrogen, $C_{1-6}$-alkyl, $C_{3-8}$-cycloalkyl, $C_{1-6}$-alkanoyl or aryl, or $R^7$ and $R^8$ together with the nitrogen atom to which they are attached form a 4 to 7 membered, saturated or unsaturated azetidinyl, pyrrolidinyl, piperidyl or azepanyl ring,
In another embodiment, f is 1.
In another embodiment, $R^1$ is $C_{1-8}$-alkyl, $C_{3-7}$-cycloalkyl-$C_{1-3}$-alkyl or $C_{3-7}$-cycloalkyl, which may optionally be substituted with one or more halogen atoms,
In still another embodiment, $R^1$ is $C_{1-8}$-alkyl, $C_{3-7}$-cycloalkyl-$C_{1-3}$-alkyl or $C_{3-7}$-cycloalkyl, such as 1-ethylpropyl, 2-propyl, cyclobutyl or cyclopentyl.
In yet another embodiment, $R^2$ is methyl.
In a further embodiment, X is —$(CH_2)_m$—$C(=O)$—$(CH_2)_o$—, —$(CH_2)_m$—, a valence bond or —$(CH_2)_m$—$CH=CH$—$(CH_2)_o$—, wherein m and o are as defined for formula (I).

In yet a further embodiment, X is —$(CH_2)_m$—$C(=O)$—, —$(CH_2)_m$—, a valence bond or —$CH=CH$—, wherein m is 1, 2, 3 or 4, such as —$(CH_2)_2$—$C(=O)$—, —$CH_2$—, —$(CH_2)_2$—, a valence bond or —$CH=CH$—.

In still a further embodiment, X is —$(CH_2)_m$—$C(=O)$—, —$(CH_2)_m$— or —$CH=CH$—, wherein m is 1, 2, 3 or 4, such as —$(CH_2)_2$—$C(=O)$—, —$CH_2$—, —$(CH_2)_2$— or —$CH=CH$—.

In another embodiment, Y is aryl, such as phenyl, which may optionally be substituted as defined for formula (I).

In still another embodiment, Y is phenyl, which may optionally be substituted with one or two of $C_{1-6}$-alkoxy, —$NR^3R^4$, halogen, trifluoromethyl or hydroxy, wherein $R^3$ and $R^4$ are as defined for formula (I), two substituents in adjacent positions forming a radical —O—$(CH_2)_{1-3}$—O—, or phenyl or phenoxy, which may optionally be substituted as defined for formula (I).

In yet another embodiment, Y is phenyl, which may optionally be substituted with one or two of $C_{1-6}$-alkoxy, —$NR^3R^4$, halogen, trifluoromethyl or hydroxy, wherein $R^3$ and $R^4$ independently are hydrogen or $C_{1-6}$-alkyl, two substituents in adjacent positions forming a radical —O—$CH_2$—O—, or phenyl or phenoxy.

In another embodiment the invention relates to a compound of the general formula ($I_1$):

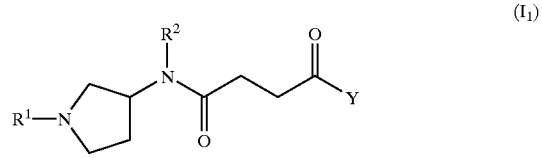

wherein $R^1$, $R^2$ and Y are as defined for formula (I) or any of the above embodiments.

In still another embodiment the invention relates to a compound of the general formula ($I_2$):

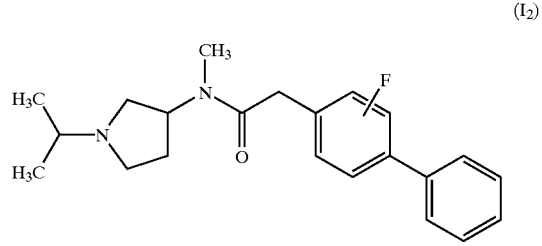

In yet another embodiment the invention relates to a compound of the general formula (I₃):

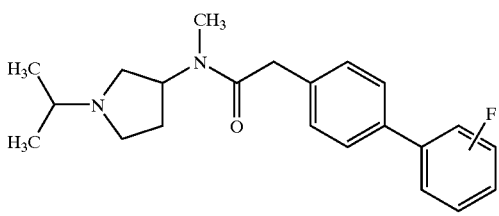

(I₃)

In still a further embodiment, the compound is selected from
4-(3,4-dimethoxyphenyl)-N-[1-(1-ethylpropyl)pyrrolidin-3-yl]-N-methyl-4-oxobutyramide,
2-(4-dimethylaminophenyl)-N-[1-(1-ethylpropyl)pyrrolidin-3-yl]-N-methylacetamide,
2-biphenyl-4-yl-N-[1-(1-ethylpropyl)pyrrolidin-3-yl]-N-methylacetamide,
4-(4-chlorophenyl)-N-[1-(1-ethylpropyl)pyrrolidin-3-yl]-N-methyl-4-oxobutyramide,
N-[1-(1-ethylpropyl)pyrrolidin-3-yl]-N-methyl-3-(4-trifluoromethylphenyl)propionamide,
N-[1-(1-ethylpropyl)pyrrolidin-3-yl]-N-methyl-3-phenoxybenzamide,
4-(3,4-dimethoxyphenyl)-N-[1-(1-ethylpropyl)pyrrolidin-3-yl]-4-oxobutyramide,
N-[1-(1-ethylpropyl)pyrrolidin-3-yl]-2-(3-fluoro-4-hydroxyphenyl)-N-methylacetamide,
2-biphenyl-4-yl-N-[1-(1-ethylpropyl)pyrrolidin-3-yl]-N-methylacetamide,
2-biphenyl-4-yl-N-(1-cyclopentylpyrrolidin-3-yl)-N-methylacetamide,
3-benzo[1,3]dioxol-5-yl-N-[1-(1-ethylpropyl)pyrrolidin-3-yl]-N-methylacrylamide,
3-(3-chlorophenyl)-N-[1-(1-ethylpropyl)pyrrolidin-3-yl]-N-methylacrylamide,
2-biphenyl-4-yl-N-(1-isopropylpyrrolidin-3-yl)-N-methylacetamide,
2-biphenyl-4-yl-N-(1-methylpyrrolidin-3-yl)-N-methylacetamide,
2-(3-fluorobiphenyl-4-yl)-N-(1-isopropylpyrrolidin-3-yl)-N-methylacetamide,
2-(2-fluorobiphenyl-4-yl)-N-(1-isopropylpyrrolidin-3-yl)-N-methylacetamide,
2-(2'-fluorobiphenyl-4-yl)-N-(1-isopropylpyrrolidin-3-yl)-N-methylacetamide,
2-(3'-fluorobiphenyl-4-yl)-N-(1-isopropylpyrrolidin-3-yl)-N-methylacetamide 2-(4'-fluorobiphenyl-4-yl)-N-(1-isopropylpyrrolidin-3-yl)-N-methylacetamide,
N-(1-Isopropylpyrrolidin-3-yl)-N-methyl-3-(4-trifluoromethylphenyl)acrylamide
2-Biphenyl-4-yl-N-(1-isopropyl-piperidin-3-yl)-N-methyl-acetamide
2-Biphenyl-4-yl-N-(1-cyclopropylmethyl-piperidin-3-yl)-N-methyl-acetamide
N-(1-Isopropyl-piperidin-3-yl)-N-methyl-3-phenoxy-benzamide
N-(1-Cyclopropylmethyl-piperidin-3-yl)-N-methyl-3-phenoxy-benzamide
3-Benzo[1,3]dioxol-5-yl-N-(1-isopropyl-piperidin-3-yl)-N-methyl-acrylamide
3-Benzo[1,3]dioxol-5-yl-N-(1-cyclopropylmethyl-piperidin-3-yl)-N-methyl-acrylamide
as well as any diastereomer or enantiomer or tautomeric form thereof including mixtures of these or a pharmaceutically acceptable salt thereof.

The compounds of the present invention may be chiral, and it is intended that any enantiomers, as separated, pure or partially purified enantiomers or racemic mixtures thereof are included within the scope of the invention.

Furthermore, when a double bond or a fully or partially saturated ring system or more than one center of asymmetry or a bond with restricted rotatability is present in the molecule diastereomers may be formed. It is intended that any diastereomers, as separated, pure or partially purified diastereomers or mixtures thereof are included within the scope of the invention.

Furthermore, some of the compounds of the present invention may exist in different tautomeric forms and it is intended that any tautomeric forms, which the compounds are able to form, are included within the scope of the present invention.

The present invention also encompasses pharmaceutically acceptable salts of the present compounds. Such salts include pharmaceutically acceptable acid addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids and the like. Further examples of pharmaceutically acceptable inorganic or organic acid addition salts include the pharmaceutically acceptable salts listed in J. Pharm. Sci. 1977, 66, 2, which is incorporated herein by reference. Examples of metal salts include lithium, sodium, potassium, magnesium salts and the like. Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like.

Also intended as pharmaceutically acceptable acid addition salts are the hydrates, which the present compounds are able to form.

The acid addition salts may be obtained as the direct products of compound synthesis. In the alternative, the free base may be dissolved in a suitable solvent containing the appropriate acid, and the salt isolated by evaporating the solvent or otherwise separating the salt and solvent.

The compounds of the present invention may form solvates with standard low molecular weight solvents using methods well known to the person skilled in the art. Such solvates are also contemplated as being within the scope of the present invention.

The invention also encompasses prodrugs of the present compounds, which on administration undergo chemical conversion by metabolic processes before becoming active pharmacological substances. In general, such prodrugs will be functional derivatives of the present compounds, which are readily convertible in vivo into the required compound of the formula (I). Conventional procedures for the selection and preparation of suitable prodrug derivatives are described, for example, in "Design of Prodrugs", ed. H. Bundgaard, Elsevier, 1985.

The invention also encompasses active metabolites of the present compounds.

The compounds of the present invention interact with the histamine H3 receptor and are accordingly useful for the treatment of a wide variety of conditions and disorders in which histamine H3 receptor interactions are beneficial.

Accordingly, in another aspect the present invention relates to a compound of the general formula (I) as well as any diastereomer or enantiomer or tautomeric form thereof including mixtures of these or a pharmaceutically acceptable salt thereof for use as a pharmaceutical composition.

The invention also relates to pharmaceutical compositions comprising, as an active ingredient, at least one compound of the formula (I) or any diastereomer or enantiomer or tautomeric form thereof including mixtures of these or a pharmaceutically acceptable salt thereof together with one or more pharmaceutically acceptable carriers or diluents.

Furthermore, the invention relates to the use of a compound of the general formula (I'):

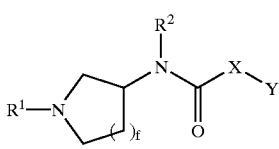

(I')

wherein
R$^1$ represents
  hydrogen,
  C$_{1-8}$-alkyl, C$_{3-8}$-alkenyl or C$_{3-8}$-alkynyl, which may optionally be substituted with one or more halogen atoms,
  C$_{3-7}$-cycloalkyl, C$_{3-7}$-cycloalkenyl, C$_{4-8}$-bicycloalkyl, C$_{3-7}$ cycloalkyl-C$_{1-3}$-alkyl or C$_{3-7}$-cycloalkenyl-C$_{1-3}$-alkyl,
  which may optionally be substituted at any position with one or more halogen atoms,
R$^2$ represents C$_{1-6}$-alkyl,
X represents —(CH$_2$)$_m$—(Z)$_n$—(CH$_2$)$_o$—,
m and o independently are 0, 1, 2, 3 or 4,
n is 0 or 1,
Z is —O—, —NH—, —N(CH$_3$)—, —C(=O)—, —CH(OH)—, —C(=N—OH)—, —S—, —S(=O)—, —S(=O)$_2$—, —CH=CH— or —C≡C—,
Y is
(a) aryl or heteroaryl, which may optionally be substituted with one or more substituents selected from
  halogen, nitro, cyano, hydroxy, C$_{1-6}$-alkanoyl, C$_{1-6}$-alkylthio, C$_{1-6}$-alkylsulfonyl, C$_{1-6}$-alkyl, C$_{1-6}$-alkoxy, C$_{3-8}$-cycloalkyl, trifluoromethyl, trifluoromethoxy, —NR$^3$R$^4$ and —O(C=O)NR$^3$R$^4$, or wherein two substituents in adjacent positions form a radical —O—(CH$_2$)$_{1-3}$—O—,
  wherein R$^3$ and R$^4$ independently are hydrogen, C$_{1-6}$-alkyl, C$_{3-8}$-cycloalkyl, C$_{1-6}$-alkanoyl or aryl, or R$^3$ and R$^4$ together with the nitrogen atom to which they are attached form a 4 to 7 membered, saturated or unsaturated azetidinyl, pyrrolidinyl, piperidyl or azepanyl ring,
  aryl, aryloxy, aryl-C$_{1-6}$-alkyl and aryl-C$_{1-6}$-alkoxy, wherein the ring moieties optionally may be substituted with one or more substituents selected from
    halogen, nitro, cyano, hydroxy, C$_{1-6}$-alkanoyl, C$_{1-6}$-alkylthio, C$_{1-6}$-alkylsulfonyl, C$_{1-6}$-alkyl, C$_{1-6}$-alkoxy, C$_{3-8}$-cycloalkyl, trifluoromethyl, trifluoromethoxy, —NR$^5$R$^6$ and —O(C=O)NR$^5$R$^6$, or wherein two substituents in adjacent positions form a radical —O—(CH$_2$)$_{1-3}$—O—,
    wherein R$^5$ and R$^6$ independently are hydrogen, C$_{1-6}$-alkyl, C$_{3-8}$-cycloalkyl, C$_{1-6}$-alkanoyl or aryl, or R$^5$ and R$^6$ together with the nitrogen atom to which they are attached form a 4 to 7 membered, saturated or unsaturated azetidinyl, pyrrolidinyl, piperidyl or azepanyl ring,
(b) C$_{3-8}$-cycloalkyl or C$_{5-8}$-cycloalkenyl, which may optionally be substituted with one or more substituents selected from
  C$_{1-6}$-alkyl, C$_{1-6}$-alkoxy, C$_{1-6}$-alkylthio, cyano, trifluoromethyl, trifluoromethoxy and halogen,
  aryl and aryloxy, wherein the ring moieties optionally may be substituted with one or more substituents selected from
    halogen, nitro, cyano, hydroxy, C$_{1-6}$-alkanoyl, C$_{1-6}$-alkylthio, C$_{1-6}$-alkylsulfonyl, C$_{1-6}$-alkyl, C$_{1-6}$-alkoxy, C$_{3-8}$-cycloalkyl, trifluoromethyl, trifluoromethoxy, —NR$^7$R$^8$ and —O(C=O)NR$^7$R$^8$, or wherein two substituents in adjacent positions form a radical —O—(CH$_2$)$_{1-3}$—O—,
    wherein R$^7$ and R$^8$ independently are hydrogen, C$_{1-6}$-alkyl, C$_{3-8}$-cycloalkyl, C$_{1-6}$-alkanoyl or aryl, or R$^7$ and R$^8$ together with the nitrogen atom to which they are attached form a 4 to 7 membered, saturated or unsaturated azetidinyl, pyrrolidinyl, piperidyl or azepanyl ring,
a well as any diastereomer or enantiomer or tautomeric form thereof including mixtures of these or a pharmaceutically acceptable salt thereof for the preparation of a pharmaceutical composition for the treatment of disorders and diseases related to the histamine H3 receptor.

In still another aspect, the invention relates to a method for the treatment of diseases and disorders related to the histamine H3 receptor the method comprising administering to a subject in need thereof an effective amount of a compound of the formula (I) or any diastereomer or enantiomer or tautomeric form thereof including mixtures of these or a pharmaceutically acceptable salt thereof or a pharmaceutical composition comprising the same.

In one aspect the invention relates to compounds with histamine H3 receptor antagonistic activity or inverse agonistic activity which may accordingly be useful in the treatment of a wide range of conditions and disorders in which histamine H3 receptor blockade is beneficial.

In another aspect the invention relates to compounds with histamine H3 receptor agonistic activity and which may accordingly be useful in the treatment of a wide range of conditions and disorders in which histamine H3 receptor activation is beneficial.

In one embodiment of the invention the present compounds are used for the preparation of a pharmaceutical composition for the reduction of weight.

In another embodiment of the invention the present compounds are used for the preparation of a pharmaceutical composition for the treatment of overweight or obesity.

In still another embodiment of the invention the present compounds are used for the preparation of a pharmaceutical composition for the suppression of appetite or satiety induction.

In a further embodiment of the invention the present compounds are used for the preparation of a pharmaceutical composition for the prevention and/or treatment of disorders and diseases related to overweight or obesity such as atherosclerosis, hypertension, IGT (impaired glucose tolerance), diabetes, especially type 2 diabetes (NIDDM (non-insulin dependent diabetes mellitus)), dyslipidaemia, coronary heart disease, gallbladder disease, osteoarthritis and various types of cancer such as endometrial, breast, prostate and colon cancers.

In yet a further embodiment of the invention the present compounds are used for the preparation of a pharmaceutical composition for the prevention and/or treatment of eating disorders such as bulimia and binge eating.

In a further embodiment of the invention the present compounds are used for the preparation of a pharmaceutical composition for the treatment of IGT.

In a further embodiment of the invention the present compounds are used for the preparation of a pharmaceutical composition for the treatment of type 2 diabetes. Such treatment includes inter alia treatment for the purpose of delaying or prevention of the progression from IGT to type 2 diabetes as well as delaying or prevention of the progression from non-insulin requiring type 2 diabetes to insulin requiring type 2 diabetes.

The compounds of the present invention may also be used for the treatment of airway disorders such as asthma, as anti-diarrhoeals and for the modulation of gastric acid secretion.

Furthermore, the compounds of the present invention may be used for the treatment of diseases associated with the regulation of sleep and wakefulness and for the treatment of narcolepsy and attention deficit disorder.

Moreover, the compounds of the invention may be used as CNS stimulants or as sedatives.

The present compounds may also be used for the treatment of conditions associated with epilepsy. Additionally, the present compounds may be used for the treatment of motion sickness and vertigo. Furthermore, they may be useful as regulators of hypothalamohypophyseal secretion, antidepressants, modulators of cerebral circulation, and in the treatment of irritable bowel syndrome.

Further, the compounds of the present invention may be used for the treatment of dementia and Alzheimer's disease.

The compounds of the present invention may also be useful for the treatment of allergic rhinitis, ulcer or anorexia.

The compounds of the present invention may furthermore be useful for the treatment of migraine, see McLeod et al., *The Journal of Pharmacology and Experimental Therapeutics* 287 (1998), 43–50, and for the treatment of myocardial infarction, see Mackins et al., *Expert Opinion on Investigational Drugs* 9 (2000), 2537–2542.

In a further aspect of the invention treatment of a patient with the present compounds is combined with diet and/or exercise.

In a further aspect of the invention the present compounds are administered in combination with one or more further active substances in any suitable ratio(s). Such further active agents may be selected from antiobesity agents, antidiabetics, antidyslipidemic agents, antihypertensive agents, agents for the treatment of complications resulting from or associated with diabetes and agents for the treatment of complications and disorders resulting from or associated with obesity.

Thus, in a further aspect of the invention the present compounds are administered in combination with one or more antiobesity agents or appetite regulating agents.

Such agents may be selected from the group consisting of CART (cocaine amphetamine regulated transcript) agonists, NPY (neuropeptide Y) antagonists, MC4 (melanocortin 4) agonists, MC3 (melanocortin 3) agonists, orexin antagonists, TNF (tumor necrosis factor) agonists, CRF (corticotropin releasing factor) agonists, CRF BP (corticotropin releasing factor binding protein) antagonists, urocortin agonists, $\beta 3$ adrenergic agonists such as CL-316243, AJ-9677, GW-0604, LY362884, LY377267 or AZ-40140, MSH (melanocyte-stimulating hormone) agonists, MCH (melanocyte-concentrating hormone) antagonists, CCK (cholecystokinin) agonists, serotonin re-uptake inhibitors such as fluoxetine, seroxat or citalopram, serotonin and noradrenaline re-uptake inhibitors, mixed serotonin and noradrenergic compounds, 5HT (serotonin) agonists, bombesin agonists, galanin antagonists, growth hormone, growth factors such as prolactin or placental lactogen, growth hormone releasing compounds, TRH (thyreotropin releasing hormone) agonists, UCP 2 or 3 (uncoupling protein 2 or 3) modulators, leptin agonists, DA agonists (bromocriptin, doprexin), lipase/amylase inhibitors, PPAR (peroxisome proliferator-activated receptor) modulators, RXR (retinoid X receptor) modulators, TR $\beta$ agonists, AGRP (Agouti related protein) inhibitors, opioid antagonists (such as naltrexone), exendin-4, GLP-1 and ciliary neurotrophic factor.

In one embodiment of the invention the antiobesity agent is leptin.

In another embodiment the antiobesity agent is dexamphetamine or amphetamine.

In another embodiment the antiobesity agent is fenfluramine or dexfenfluramine.

In still another embodiment the antiobesity agent is sibutramine.

In a further embodiment the antiobesity agent is orlistat.

In another embodiment the antiobesity agent is mazindol or phentermine.

In still another embodiment the antiobesity agent is phendimetrazine, diethylpropion, fluoxetine, bupropion, topiramate or ecopipam.

In yet another embodiment the antiobesity agent is growth hormone, a growth factor such as prolactin or placental lactogen, or a growth hormone releasing compound.

In yet a further aspect the present compounds are administered in combination with one or more antidiabetic agents.

Relevant antidiabetic agents include insulin, insulin analogues and derivatives such as those disclosed in EP 0 792 290 (Novo Nordisk A/S), eg $N^{\epsilon B29}$-tetradecanoyl des (B30) human insulin, EP 0 214 826 and EP 0 705 275 (Novo Nordisk A/S), eg $Asp^{B28}$ human insulin, U.S. Pat. No. 5,504,188 (Eli Lilly), eg $Lys^{B28}$ $Pro^{B29}$ human insulin, EP 0 368 187 (Aventis), eg Lantus®, which are all incorporated herein by reference, GLP-1 derivatives such as those disclosed in WO 98/08871 (Novo Nordisk A/S), which is incorporated herein by reference, as well as orally active hypoglycaemic agents.

The orally active hypoglycaemic agents preferably comprise imidazolines, sulfonylureas, biguamides, meglitinides, oxadiazolidinediones, thiazolidinediones, insulin sensitizers, α-glucosidase inhibitors, agents acting on the ATP-dependent potassium channel of the β-cells eg potassium channel openers such as those disclosed in WO 97/26265, WO 99/03861 and WO 00/37474 (Novo Nordisk A/S) which are incorporated herein by reference, or mitiglinide, or a potassium channel blocker, such as BTS-67582, nateglinide, glucagon antagonists such as those disclosed in WO 99/01423 and WO 00/39088 (Novo Nordisk A/S and Agouron Pharmaceuticals, Inc.), which are incorporated herein by reference, GLP-1 agonists such as those disclosed in WO 00/42026 (Novo Nordisk A/S and Agouron Pharmaceuticals, Inc.), which are incorporated herein by reference, DPP-IV (dipeptidyl peptidase-IV) inhibitors, PTPase (protein tyrosine phosphatase) inhibitors, inhibitors of hepatic enzymes involved in stimulation of gluconeogenesis and/or glycogenolysis, glucose uptake modulators, GSK-3 (glycogen synthase kinase-3) inhibitors, compounds modifying the lipid metabolism such as antilipidemic agents, compounds lowering food intake, PPAR (peroxisome proliferator-activated receptor) and RXR (retinoid X receptor) agonists, such as ALRT-268, LG-1268 or LG-1069.

In one embodiment of the invention the present compounds are administered in combination with insulin or an insulin analogue or derivative, such as $N^{\epsilon B29}$-tetradecanoyl des (B30) human insulin, $Asp^{B28}$ human insulin, $Lys^{B28}$ $Pro^{B29}$ human insulin, Lantus®, or a mix-preparation comprising one or more of these.

In a further embodiment of the invention the present compounds are administered in combination with a sulfonylurea eg tolbutamide, chlorpropamide, tolazamide, glibenclamide, glipizide, glimepiride, gliclazide or glyburide.

In another embodiment of the invention the present compounds are administered in combination with a biguamide eg metformin.

In yet another embodiment of the invention the present compounds are administered in combination with a meglitinide eg repaglinide or nateglinide.

In still another embodiment of the invention the present compounds are administered in combination with a thiazolidinedione insulin sensitizer eg troglitazone, ciglitazone, pioglitazone, rosiglitazone, isaglitazone, darglitazone, englitazone, CS-011/CI-1037 or T 174 or the compounds disclosed in WO 97/41097, WO 97/41119, WO 97/41120, WO 00/41121 and WO 98/45292 (Dr. Reddy's Research Foundation), which are incorporated herein by reference.

In still another embodiment of the invention the present compounds may be administered in combination with an insulin sensitizer eg such as GI 262570, YM-440, MCC-555, JTT-501, AR-H039242, KRP-297, GW-409544, CRE-16336, AR-H049020, LY510929, MBX-102, CLX-0940, GW-501516 or the compounds disclosed in WO 99/19313, WO 00/50414, WO 00/63191, WO 00/63192, WO 00/63193 (Dr. Reddy's Research Foundation) and WO 00/23425, WO 00/23415, WO 00/23451, WO 00/23445, WO 00/23417, WO 00/23416, WO 00/63153, WO 00/63196, WO 00/63209, WO 00/63190 and WO 00/63189 (Novo Nordisk A/S), which are incorporated herein by reference.

In a further embodiment of the invention the present compounds are administered in combination with an α-glucosidase inhibitor eg voglibose, emiglitate, miglitol or acarbose.

In another embodiment of the invention the present compounds are administered in combination with an agent acting on the ATP-dependent potassium channel of the β-cells eg tolbutamide, glibenclamide, glipizide, gliclazide, BTS-67582 or repaglinide.

In yet another embodiment of the invention the present compounds may be administered in combination with nateglinide.

In still another embodiment, the present compounds are administered in combination with an antihyperlipidemic agent or antilipidemic agent, eg cholestyramine, colestipol, clofibrate, gemfibrozil, lovastatin, pravastatin, simvastatin, probucol or dextrothyroxine.

In still another embodiment of the invention the present compounds are administered in combination with an antilipidemic agent eg cholestyramine, colestipol, clofibrate, gemfibrozil, lovastatin, pravastatin, simvastatin, probucol or dextrothyroxine.

In another aspect of the invention, the present compounds are administered in combination with more than one of the above-mentioned compounds eg in combination with metformin and a sulfonylurea such as glyburide; a sulfonylurea and acarbose; nateglinide and metformin; acarbose and metformin; a sulfonylurea, metformin and troglitazone; insulin and a sulfonylurea; insulin and metformin; insulin, metformin and a sulfonylurea; insulin and troglitazone; insulin and lovastatin; etc.

Furthermore, the present compounds may be administered in combination with one or more antihypertensive agents. Examples of antihypertensive agents are β-blockers such as alprenolol, atenolol, timolol, pindolol, propranolol and metoprolol, ACE (angiotensin converting enzyme) inhibitors such as benazepril, captopril, enalapril, fosinopril, lisinopril, quinapril and ramipril, calcium channel blockers such as nifedipine, felodipine, nicardipine, isradipine, nimodipine, diltiazem and verapamil, and α-blockers such as doxazosin, urapidil, prazosin and terazosin. Further reference can be made to Remington: The Science and Practice of Pharmacy, $19^{th}$ Edition, Gennaro, Ed., Mack Publishing Co., Easton, Pa., 1995.

It should be understood that any suitable combination of the compounds according to the invention with diet and/or exercise, one or more of the above-mentioned compounds and optionally one or more other active substances are considered to be within the scope of the present invention.

Pharmaceutical Compositions

The compounds of the invention may be administered alone or in combination with pharmaceutically acceptable carriers or excipients, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, $19^{th}$ Edition, Gennaro, Ed., Mack Publishing Co., Easton, Pa., 1995.

The pharmaceutical compositions may be specifically formulated for administration by any suitable route such as the oral, rectal, nasal, pulmonary, topical (including buccal and sublingual), transdermal, intracisternal, intraperitoneal, vaginal and parenteral (including subcutaneous, intramuscular, intrathecal, intravenous and intradermal) route, the oral route being preferred. It will be appreciated that the preferred route will depend on the general condition and age of the subject to be treated, the nature of the condition to be treated and the active ingredient chosen.

Pharmaceutical compositions for oral administration include solid dosage forms such as capsules, tablets, dragees, pills, lozenges, powders and granules. Where appropriate, they can be prepared with coatings such as enteric coatings or they can be formulated so as to provide controlled release of the active ingredient such as sustained or prolonged release according to methods well known in the art.

Liquid dosage forms for oral administration include solutions, emulsions, suspensions, syrups and elixirs.

Pharmaceutical compositions for parenteral administration include sterile aqueous and non-aqueous injectable solutions, dispersions, suspensions or emulsions as well as sterile powders to be reconstituted in sterile injectable solutions or dispersions prior to use. Depot injectable formulations are also contemplated as being within the scope of the present invention.

Other suitable administration forms include suppositories, sprays, ointments, cremes, gels, inhalants, dermal patches, implants etc.

A typical oral dosage is in the range of from about 0.001 to about 100 mg/kg body weight per day, preferably from about 0.01 to about 50 mg/kg body weight per day, and more preferred from about 0.05 to about 10 mg/kg body weight per day administered in one or more dosages such as 1 to 3 dosages. The exact dosage will depend upon the frequency and mode of administration, the sex, age, weight and general condition of the subject treated, the nature and severity of the condition treated and any concomitant diseases to be treated and other factors evident to those skilled in the art.

The formulations may conveniently be presented in unit dosage form by methods known to those skilled in the art. A typical unit dosage form for oral administration one or more times per day such as 1 to 3 times per day may contain of from 0.05 to about 1000 mg, preferably from about 0.1 to about 500 mg, and more preferred from about 0.5 mg to about 200 mg.

For parenteral routes, such as intravenous, intrathecal, intramuscular and similar administration, typically doses are in the order of about half the dose employed for oral administration.

The compounds of this invention are generally utilized as the free substance or as a pharmaceutically acceptable salt thereof. One example is an acid addition salt of a compound having the utility of a free base. When a compound of the formula (I) contains a free base such salts are prepared in a conventional manner by treating a solution or suspension of a free base of the formula (I) with a chemical equivalent of a pharmaceutically acceptable acid, for example, inorganic and organic acids. Representative examples are mentioned above. Physiologically acceptable salts of a compound with a hydroxy group include the anion of said compound in combination with a suitable cation such as sodium or ammonium ion.

For parenteral administration, solutions of the novel compounds of the formula (I) in sterile aqueous solution, aqueous propylene glycol or sesame or peanut oil may be employed. Such aqueous solutions should be suitable buffered if necessary and the liquid diluent first rendered isotonic with sufficient saline or glucose. The aqueous solutions are particularly suitable for intravenous, intramuscular, subcutaneous and intraperitoneal administration. The sterile aqueous media employed are all readily available by standard techniques known to those skilled in the art.

Suitable pharmaceutical carriers include inert solid diluents or fillers, sterile aqueous solution and various organic solvents. Examples of solid carriers are lactose, terra alba, sucrose, cyclodextrin, talc, gelatine, agar, pectin, acacia, magnesium stearate, stearic acid or lower alkyl ethers of cellulose. Examples of liquid carriers are syrup, peanut oil, olive oil, phospholipids, fatty acids, fatty acid amines, polyoxyethylene or water. Similarly, the carrier or diluent may include any sustained release material known in the art, such as glyceryl monostearate or glyceryl distearate, alone or mixed with a wax. The pharmaceutical compositions formed by combining the novel compounds of the formula (I) and the pharmaceutically acceptable carriers are then readily administered in a variety of dosage forms suitable for the disclosed routes of administration. The formulations may conveniently be presented in unit dosage form by methods known in the art of pharmacy.

Formulations of the present invention suitable for oral administration may be presented as discrete units such as capsules or tablets, each containing a predetermined amount of the active ingredient, and which may include a suitable excipient. These formulations may be in the form of powder or granules, as a solution or suspension in an aqueous or non-aqueous liquid, or as an oil-in-water or water-in-oil liquid emulsion.

If a solid carrier is used for oral administration, the preparation may be tabletted, placed in a hard gelatine capsule in powder or pellet form or it can be in the form of a troche or lozenge. The amount of solid carrier will vary widely but will usually be from about 25 mg to about 1 g. If a liquid carrier is used, the preparation may be in the form of a syrup, emulsion, soft gelatine capsule or sterile injectable liquid such as an aqueous or non-aqueous liquid suspension or solution.

A typical tablet, which may be prepared by conventional tabletting techniques, may contain:

| Core: | |
|---|---|
| Active compound (as free compound or salt thereof) | 5.0 mg |
| Lactosum Ph. Eur. | 67.8 mg |
| Cellulose, microcryst. (Avicel) | 31.4 mg |
| Amberlite ® IRP88* | 1.0 mg |
| Magnesii stearas Ph. Eur. | q.s. |
| Coating: | |
| Hydroxypropyl methylcellulose | approx. 9 mg |
| Mywacett 9–40 T** | approx. 0.9 mg |

*Polacrillin potassium NF, tablet disintegrant, Rohm and Haas.
**Acylated monoglyceride used as plasticizer for film coating.

If desired, the pharmaceutical composition of the invention may comprise the compound of the formula (I) in combination with further pharmacologically active substances such as those described in the foregoing.

EXAMPLES

In the examples the following terms are intended to have the following, general meanings:

DCM: dichloromethane
DIPEA: diisopropylethylamine
DMF: N,N-dimethylformamide
DMSO: dimethyl sulphoxide
THF: tetrahydrofuran
NMR spectra were recorded on Bruker 300 MHz and 400 MHz instruments. HPLC-MS was performed on a Perkin Elmer instrument (API 100). The column used was X-Terra C18, 5 μm, 50×3 mm, and elution was done at 1.5 ml/min at room temperature with a gradient of 5% to 90% acetonitrile in water with 0.01% trifluoroacetic acid within 7.5 min.

General Procedure (A)

The compounds of formula (I) can be prepared according to the following general procedure (A):

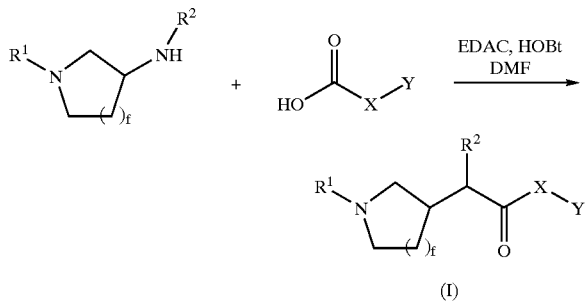

To a mixture of the acid (150 mmol), DMF (200 ml), and N-hydroxybenzotriazole (40.6 g, 301 mmol) is added a solution of N-ethyl-N'-(3-dimethylaminopropyl) carbodiimide hydrochloride (28.8 g, 150 mmol) in DMF (100 ml). The mixture was stirred at room temperature for 1.5 hour, and a solution of the diamine (150 mmol) in DCM (100 ml) is added. The mixture is stirred at room temperature for 4 hours, concentrated under reduced pressure, and the residue is distributed between ethyl acetate (1.0 l) and a saturated, aqueous NaHCO$_3$ solution (1.0 l). The phases are separated, the organic layer is dried (MgSO$_4$), and concentrated, and the residue is re-dissolved in 1 M aqueous hydrochloric acid (150 ml). The solution is concentrated, and the residue is dried by co-evaporation with ethanol. Re-crystallization of the residue from ethanol yielded the compound of formula (Ia).

Example 1

General Procedure (A)

4-(3,4-Dimethoxyphenyl)-N-[1-(1-ethylpropyl)pyrrolidin-3-yl]-N-methyl-4-oxobutyramide Hydrochloride

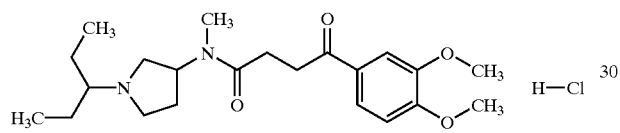

$^1$H NMR (DMSO-d$_6$) δ0.92 (m, 6H), 1.70 (m, 4H), 1.95–2.30 (m, 2H), 2.52–3.65 (m, 12H), 3.80 (s, 3H), 3.84 (s, 3H), 4.90–5.20 (m, 1H), 7.07 (d, J=8 Hz, 1H), 7.45 (br s, 1H), 7.68 (br d, J=8 Hz, 1H), 10.70 (m, 1H); HPLC-MS: m/z 391 (MH$^+$); Rf: 2.40 min.

Example 2

General Procedure (A)

2-(4-Dimethylaminophenyl)-N-[1-(1-ethylpropyl)pyrrolidin-3-yl]-N-methylacetamide Hydrochloride

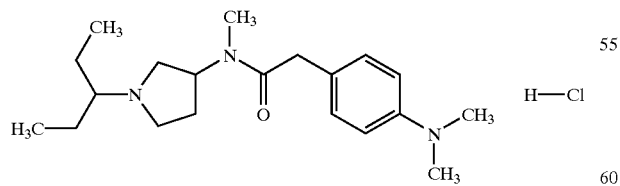

$^1$H NMR (DMSO-d$_6$) δ 0.90 (m, 6H), 1.70 (m, 4H), 1.95–2.18 (m, 2H), 2.75–3.90 (m, 16H), 4.90–5.20 (m, 1H), 7.27–7.60 (m, 4H), 10.40–11.20 (m, 1H); HPLC-MS: m/z 332 (MH$^+$); Rf: 1.73 min.

Example 3

General Procedure (A)

2-Biphenyl-4-yl-N-[1-(1-ethylpropyl)pyrrolidin-3-yl]-N-methylacetamide Hydrochloride

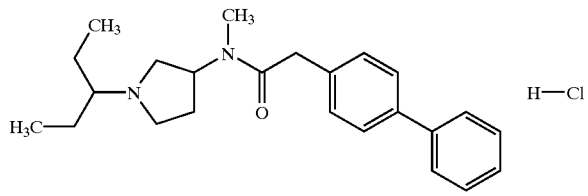

$^1$H NMR (DMSO-d$_6$) δ 0.90 (m, 6H), 1.70 (m, 4H), 1.96–2.20 (m, 2H), 2.75–3.90 (m, 10H), 4.90–5.15 (m, 1H), 7.29–7.40 (m, 3H), 7.46 (t, J=8 Hz, 2H), 7.59–7.68 (m, 4H), 10.10–10.90 (m, 1H); HPLC-MS: m/z 365 (MH$^+$); Rf: 3.77 min.

Example 4

General Procedure (A)

4-(4-Chlorophenyl)-N-[1-(1-ethylpropyl)pyrrolidin-3-yl]-N-methyl-4-oxobutyramide Hydrochloride

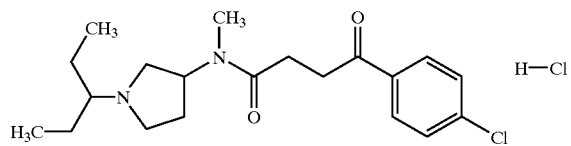

$^1$H NMR (DMSO-d$_6$) δ0.90 (m, 6H), 1.70 (m, 4H), 1.95–2.20 (m, 2H), 2.67–3.63 (m, 12H), 4.85–5.15 (m, 1H), 7.59 (d, J=8 Hz, 2H), 7.99 (d, J=8 Hz, 2H), 10.3–11.1 (m, 1H); HPLC-MS: m/z 367 (MH$^+$); Rf: 3.00 min.

Example 5

General Procedure (A)

N-[1-(1-Ethylpropyl)pyrrolidin-3-yl]-N-methyl-3-(4-trifluoromethylphenyl)propionamide Hydrochloride

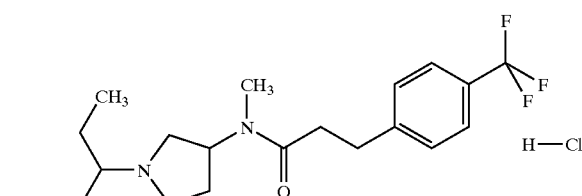

$^1$H NMR (DMSO-d$_6$) δ 0.90 (m, 6H), 1.70 (m, 4H), 1.90–2.20 (m, 2H), 2.67–3.63 (m, 12H), 4.78–5.22 (m, 1H), 7.49 (m, 2H), 7.63 (d, J=8 Hz, 2H), 10.4–11.1 (m, 1H); HPLC-MS: m/z 372 (MH$^+$); Rf: 3.50 min.

Example 6

General Procedure (A)

N-[1-(1-Ethylpropyl)pyrrolidin-3-yl]-N-methyl-3-phenoxybenzamide Hydrochloride

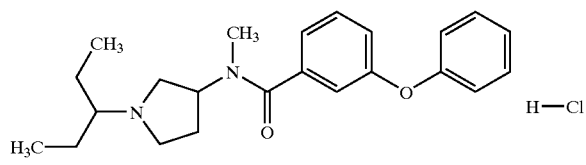

$^1$H NMR (DMSO-$d_6$) δ 0.90 (m, 6H), 1.70 (m, 4H), 2.00–2.30 (m, 2H), 2.85–3.70 (m, 8H), 4.45–5.20 (m, 1H), 6.90–7.21 (m, 6H), 7.40–7.50 (m, 3H), 10.2–11.0 (m, 1H); HPLC-MS: m/z 368 (MH$^+$); Rf: 3.33 min.

Example 7

General Procedure (A)

4-(3,4-Dimethoxyphenyl)-N-[1-(1-ethylpropyl)pyrrolidin-3-yl]-4-oxobutyramide Hydrochloride

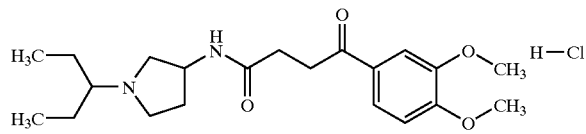

$^1$H NMR (DMSO-$d_6$) δ 0.93 (br t, J=7 Hz, 6H), 1.69 (m, 4H), 1.90 (m, 1H), 2.10–2.35 (m, 1H), 2.47 (t, J=7 Hz, 2H), 2.92 (m, 0.5H), 3.12 (m, 1H), 3.23 (t, J=7 Hz, 2H), 3.25–3.70 (m, 3.5H), 3.81 (s, 3H), 3.84 (s, 3H), 4.35 (m, 1H), 7.07 (d, J=8 Hz, 1H), 7.44 (m, 1H), 7.68 (dd, J=1 Hz, 8 Hz, 1H), 8.41 (d, J=7 Hz, 0.5H), 8.52 (d, J=7 Hz, 0.5H), 10.35 (m, 1H); HPLC-MS: m/z 377 (MH$^+$); Rf: 1.79 min.

Example 8

General Procedure (A)

N-[1-(1-Ethylpropyl)pyrrolidin-3-yl]-2-(3-fluoro-4-hydroxyphenyl)-N-methylacetamide Hydrochloride

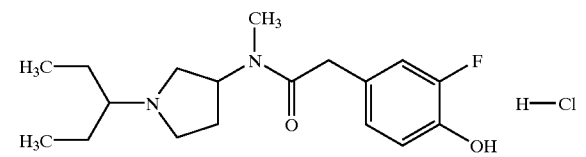

$^1$H NMR (DMSO-$d_6$) δ 0.90 (m, 6H), 1.70 (m, 4H), 1.90–2.20 (m, 2H), 2.70–3.25 (m, 10H), 4.85–5.15 (m, 1H), 6.78–7.10 (m, 3H), 9.70 (br s, 1H), 10.25–11.05 (m, 1H); HPLC-MS: m/z 323 (MH$^+$); Rf: 1.63 min.

Example 9

General Procedure (A)

2-Biphenyl-4-yl-N-[1-(1-ethylpropyl)pyrrolidin-3-yl]-N-methylacetamide Hydrochloride

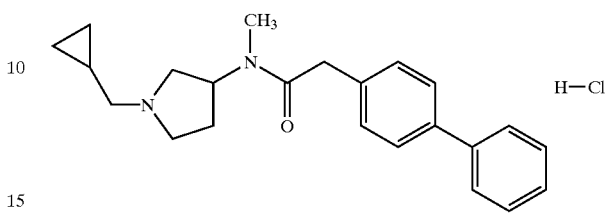

$^1$H NMR (DMSO-$d_6$) δ0.38 (m, 2H), 0.59 (m, 2H), 1.07 (m, 1H), 2.00–2.25 (m, 2H), 2.70–4.00 (m, 11H), 4.88–5.09 (m, 1H), 7.29–7.38 (m, 3H), 7.46 (t, J=8 Hz, 2H), 7.59–7.66 (m, 4H), 10.55–11.30 (m, 1H); HPLC-MS: m/z 349 (MH$^+$); Rf: 2.94 min.

Example 10

General Procedure (A)

2-Biphenyl-4-yl-N-(1-cyclopentylpyrrolidin-3-yl)-N-methylacetamide Hydrochloride

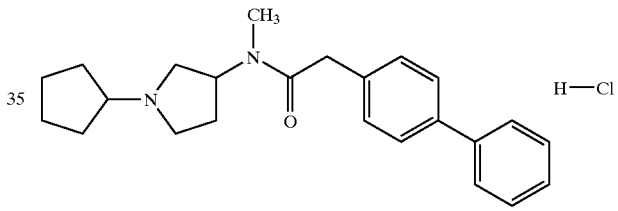

$^1$H NMR (DMSO-$d_6$) δ 1.53 (m, 2H), 1.72 (m, 4H), 1.85–2.19 (m, 4H), 2.70–4.00 (m, 10H), 4.85–5.29 (m, 1H), 7.29–7.38 (m, 3H), 7.46 (t, J=8 Hz, 2H), 7.59–7.66 (m, 4H), 10.90–11.60 (m, 1H); HPLC-MS: m/z 363 (MH$^+$); Rf: 2.86 min.

Example 11

General Procedure (A)

3-Benzo[1,3]dioxol-5-yl-N-[1-(1-ethylpropyl)pyrrolidin-3-yl]-N-methylacrylamide Hydrochloride

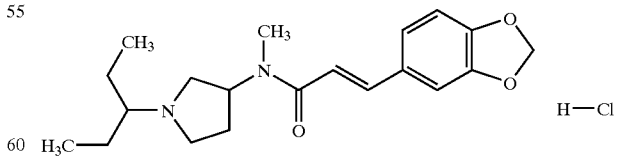

$^1$H NMR (DMSO-$d_6$) δ0.90 (m, 6H), 1.73 (m, 4H), 2.05–2.25 (m, 2H), 2.80–4.05 (m, 8H), 5.05–5.22 (m, 1H), 6.07 (s, 2H), 6.91–7.18 (m, 3H), 7.40–7.47 (m, 2H), 10.40–11.20 (m, 1H); HPLC-MS: m/z 345 (MH$^+$); Rf: 2.36 min.

Example 12

General Procedure (A)

3-(3-Chlorophenyl)-N-[1-(1-ethylpropyl)pyrrolidin-3-yl]-N-methylacrylamide Hydrochloride

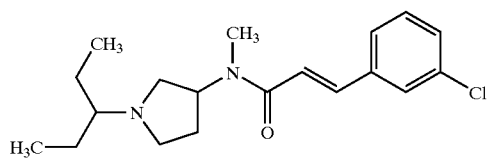

$^1$H NMR (DMSO-d$_6$) δ0.90 (m, 6H), 1.73 (m, 4H), 2.05–2.30 (m, 2H), 2.85–3.70 (m, 8H), 5.05–5.22 (m, 1H), 7.21–7.52 (m, 4H), 7.68 (br s, 1H), 7.89 (br s, 1H), 10.20–11.05 (m, 1H); HPLC-MS: m/z 335 (MH$^+$); Rf: 3.07 min.

Example 13

General Procedure (A)

2-Biphenyl-4-yl-N-(1-isopropylpyrrolidin-3-yl)-N-methylacetamide Hydrochloride

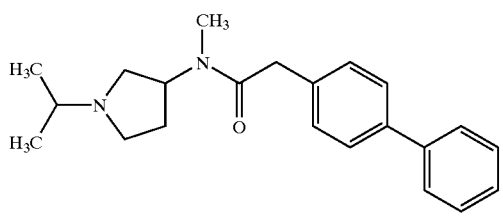

$^1$H NMR (DMSO-d$_6$) δ 1.28 (d, J=7 Hz, 6H), 1.95–2.20 (m, 2H), 2.76–3.87 (m, 10H), 4.92–5.25 (m, 1H), 7.29–7.38 (m, 3H), 7.46 (t, J=8 Hz, 2H), 7.59–7.66 (m, 4H), 10.80–11.50 (m, 1H); HPLC-MS: m/z 337 (MH$^+$); Rf: 3.07 min.

Example 14

General Procedure (A)

2-Biphenyl-4-yl-N-(1-cyclobutylpyrrolidin-3-yl)-N-methylacetamide Hydrochloride

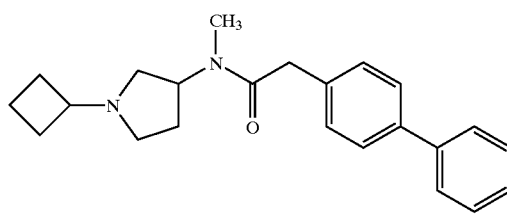

$^1$H NMR (DMSO-d$_6$) δ1.64–1.86 (m, 2H), 1.95–2.40 (m, 6H), 2.70–3.85 (m, 10H), 4.80–5.25 (m, 1H), 7.29–7.38 (m, 3H), 7.46 (t, J=8 Hz, 2H), 7.59–7.66 (m, 4H), 11.20–11.80 (m, 1H); HPLC-MS: m/z 349 (MH$^+$); Rf: 3.07 min.

Example 15

General Procedure (A))

2-Biphenyl-4-yl-N-(1-methylpyrrolidin-3-yl)-N-methylacetamide Hydrochloride

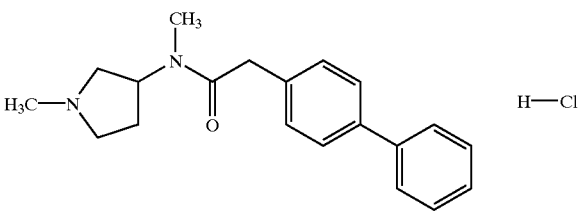

$^1$H NMR (DMSO-d$_6$) δ 1.93–2.30 (m, 2H), 2.73–2.87 (m, 3H), 2.90–3.68 (m, 7H), 3.70–3.90 (m, 2H), 4.85–5.15 (m, 1H), 7.32–7.40 (m, 3H), 7.44 (t, J=8 Hz, 2H), 7.59–7.66 (m, 4H), 10.80–11.60 (m, 1H); HPLC-MS: m/z 309 (MH$^+$); Rf: 3.27 min.

Example 16

General Procedure (A))

2-(2-Fluorobiphenyl-4-yl)-N-(1-isopropylpyrrolidin-3-yl)-N-methylacetamide Hydrochloride

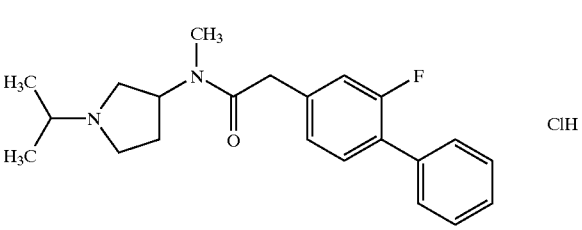

$^1$H NMR (DMSO-d$_6$) δ 1.28 (d, J=7 Hz, 6H), 2.09 (m, 2H), 2.82 (m, 1H), 3.04 (m, 4H), 3.20–3.63 (m, 3H), 3.78–3.88 (m, 2H), 4.93 (m, 0.5H), 5.18 (m, 0.5H), 7.25–7.55 (m, 8H), 10.70–11.45 (m, 1H); HPLC-MS: m/z 355 (MH$^+$); Rf: 3.60 min.

Example 17

General Procedure (A)

N-(1-Isopropylpyrrolidin-3-yl)-N-methyl-3-(4-trifluoromethylphenyl)acrylamide Hydrochloride

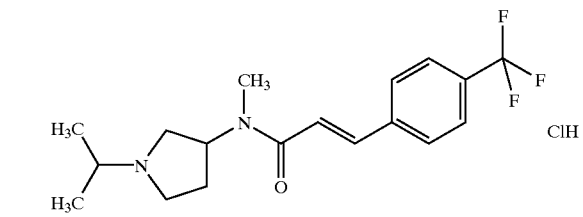

$^1$H NMR (DMSO-d$_6$) δ1.31 (d, J=7 Hz, 6H), 2.13 (m, 2H), 2.88–3.70 (m, 8H), 5.00–5.40 (m, 1H), 7.28–7.61 (m, 2H), 7.78 (m, 2H), 7.97 (m, 2H), 10.95–11.75 (m, 1H); HPLC-MS: m/z 341 (MH$^+$); Rf: 3.47 min.

Example 18

General Procedure (A)
2-Biphenyl-4-yl-N-(1-isopropyl-piperidin-3-yl)-N-methyl-acetamide Hydrochloride

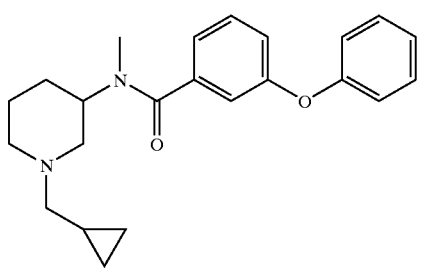

¹H NMR (DMSO-d₆) δ 1.26 (d, J=7 Hz, 3H), 1.30 (d, J=7 Hz, 3H), 1.38 (m, 1H), 2.7–3.55 (m, 11H), 3.65–4.05 (m, 2H), 4.75 (m, 1H), 7.34 (dd, 2H), 7.4–7.54 (m, 3H), 7.55–7.69 (m, 4H), 10.03 (s, 0.5H), 11.09 (s, 0.5H);
C23H30N2O, HCl+1.25 mol H2O

| Calc.: | C 67.15 | H 8.18 | N 6.54 |
|---|---|---|---|
| Found.: | C 67.46 | H 8.25 | N 6.84. |

Example 19

General Procedure (A)
2-Biphenyl-4-yl-N-(1-cyclopropylmethyl-piperidin-3-yl)-N-methyl-acetamide Hydrochloride

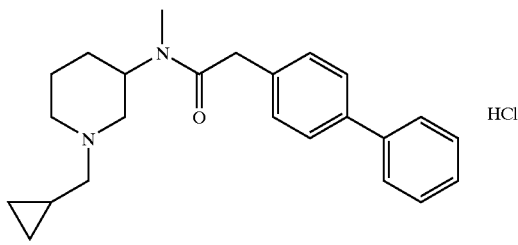

¹H NMR (DMSO-d₆) δ0.38 (m, 2H), 0.63 (m, 2H), 1.14 (m, 1H), 1.35–2.02 (m, 4H), 2.65–3.55 (m, 9H), 3.71–4.02 (m, 2H), 4.70 (m, 1H), 7.33 (dd, 2H), 7.42–7.52 (m, 3H), 7.57–7.68 (m, 4H), 10.38 (broad s, 0.5H), 11.30 (broad s, 0.5H); HPLC-MS: m/z 363 (MH⁺); Rf: 3.70 min.

Example 20

General Procedure (A)
N-(1-Isopropyl-piperidin-3-yl)-N-methyl-3-phenoxy-benzamide Hydrochloride

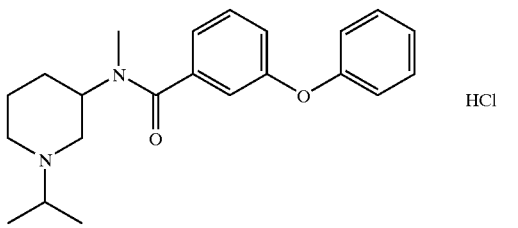

¹H NMR (CDCl₃) of the free base δ 1.00 (m, 6H), 1.3–1.9 (m, 4H), 1.97 (t, 1H), 2.22 (t, 1H), 2.6–3.0 (m, 6H), 3.60–3.83 (m, 1H), 6.9–7.16 (m, 6H), 7.30–7.40 (m, 3H); HPLC-MS: m/z 353 (MH⁺); Rf: 2.78 min.

Example 21

General Procedure (A)

N-(1-Cyclopropylmethyl-piperidin-3-yl)-N-methyl-3-phenoxy-benzamide Hydrochloride

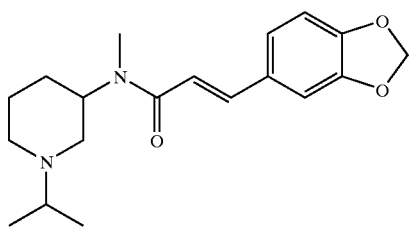

¹H NMR (CDCl₃) δ0.45 (m, 2H), 0.81 (m, 2H), 1.30 (m, 1H), 2.02 (m, 2H), 2.2–2.55 (m, 3H), 2.71 (m, 1H), 2.93 (dd, 2H), 3.06 (s, 3H), 3.63 (m, 2H), 3.88 (m, 0.5H), 4.15 (m, 0.5H), 6.95–7.10 (m, 5H), 7.15 (t, 1H), 7.33–7.42 (m, 3H), 12.10 (broad s, 1H); HPLC-MS: m/z 365 (MH⁺); Rf: 2.80 min.

Example 22

General Procedure (A)

3-Benzo[1,3]dioxol-5-yl-N-(1-isopropyl-piperidin-3-yl)-N-methyl-acrylamide Hydrochloride ¹H NMR (CDCl₃) δ1.45 (m, 6H), 1.8–2.15 (m, 4H), 2.35–2.85 (m, 3H), 2.95 (m, 1H), 3.20–3.55 (m, 4H), 3.96 (m, 0.5H), 4.15 (m, 0.5H), 5.38 (m, 0.5H), 6.00 (broad s, 2H), 6.60 (m, 0.5H), 6.81 (d, J=8 Hz, 1H), 7.02 (m, 1H), 7.27–7.75 (m, 2H), 11.85 (broad s, 0.5H), 12.75 (broad s, 0.5H); HPLC-MS: m/z 331 (MH⁺); Rf: 2.11 min.

Example 23

General Procedure (A)

3-Benzo[1,3]dioxol-5-yl-N-(1-cyclopropylmethyl-piperidin-3-yl)-N-methylacrylamide Hydrochloride

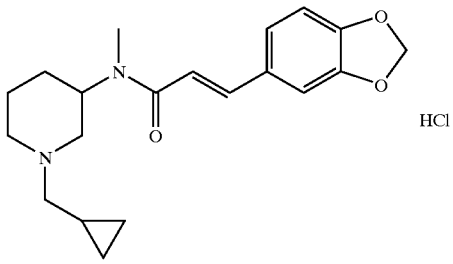

$^1$H NMR (CDCl$_3$) δ 0.45 (m, 2H), 0.80 (d, 2H), 1.31 (m, 1H), 1.70–2.15 (m, 4H), 2.27–3.36 (m, 8H), 3.38–4.15 (m, 3H), 5.23 (m, 0.5H), 6.00 (m, 2H), 6.60 (m, 0.5H), 6.81 (d, J=8 Hz, 1H), 6.94–7.09 (m, 1H), 7.27–7.75 (m, 2H), 12.13 (broad s, 0.5H), 12.97 (broad s, 0.5H);

HPLC-MS: m/z 343 (MH$^+$); Rf: 2.22 min.

Pharmacological Methods

The ability of the compounds to interact with the histamine H3 receptor can be determined by the following in vitro binding assays.

Binding Assay I

The H3-receptor agonist ligand R-α-methyl[$^3$H]histamine (RAMHA) is incubated with isolated rat cortex cell-membranes at 25° C. for 1 hour, followed by a filtration of the incubate through Whatman GF/B filters. Radioactivity retained on the filters is measured using a beta counter.

Male Wistar rats (150–200 g) are decapitated and cerebral cortex is quickly dissected out and frozen immediately on dry ice. Tissue is kept at −80° C. until membrane preparation. During the membrane preparation the tissue is kept on ice all the time. Rat cerebral cortex is homogenized in 10 volumes (w/w) ice-cold Hepes buffer (20 mM Hepes, 5 mM MgCl$_2$ pH 7.1 (KOH)+1 mg/ml bacitracin) using an Ultra-Turrax homogenizer for 30 seconds. The homogenate is centrifuged at 140 g in 10 min. The supernatant is transferred to a new test tube and centrifuged for 30 min at 30 000 g. Pellet is resuspended in 5–10 ml Hepes buffer, homogenized and centrifuged for 10 min at 30 000 g. This short centrifugation step is repeated twice. After the last centrifugation the pellet is resuspended in 2–4 ml Hepes buffer and the protein concentration is determined. The membranes are diluted to a protein concentration of 5 mg/ml using Hepes buffer, aliquoted and stored at −80° C. until use.

50 μl test-compound, 100 μl membrane (200 μg/ml), 300 μl Hepes buffer and 50 μl R-α-methyl[$^3$H]histamine (1 nM) are mixed in a test tube. The compounds to be tested are dissolved in DMSO and further diluted in H$_2$O to the desired concentrations. Radioligand and membranes are diluted in Hepes buffer+1 mg/ml bacitracin. The mixture is incubated for 60 min at 25° C. Incubation is terminated by adding 5 ml ice-cold 0.9% NaCl, followed by rapid filtration through Whatman GF/B filters pre-treated for 1 hour with 0.5% polyethyleneimine. The filters are washed with 2×5 ml ice-cold NaCl. To each filter a 3 ml scintillation cocktail is added and the radioactivity retained is measured with a Packard Tri-Carb beta counter.

IC$_{50}$ values are calculated by non-linear regression analysis of binding curves (6 points minimum) using the windows program GraphPad Prism, GraphPad software, USA.

Binding Assay II

The human H3 receptor is cloned by PCR and subcloned into the pcDNA3 expression vector. Cells stably expressing the H3 receptor are generated by transfecting the H3-expression vectors into HEK 293 cells and using G418 to select for H3 clones. The human H3-HEK 293 clones are cultured in DMEM (GIBCO-BRL) with glutamax, 10% foetal calf serum, 1% penicillin/streptavidin and 1 mg/ml G 418 at 37° C. and 5% CO$_2$. Before harvesting, the confluent cells are rinsed with PBS and incubated with Versene (proteinase, GIBCO-BRL) for approximately 5 min. The cells are flushed with PBS and DMEM and the cell suspension collected in a tube and centrifuged for 5–10 min at 420 g in a Heraeus Sepatech Megafuge 1.0. The pellet is resuspended in 10–20 vol. Hepes buffer (20 mM Hepes, 5 mM MgCl$_2$, pH 7.1 (KOH)) and homogenized for 10–20 seconds using an Ultra-Turrax homogenizer. The homogenate is centrifuged for 30 min at 30 000 g. The pellet is resuspended in 5–10 ml Hepes buffer, homogenized 5–10 seconds with the Ultra-Turrax and centrifuged for 10 min at 30 000 g. Following this centrifugation step, the membrane pellet is resuspended in 2–4 ml Hepes buffer, homogenized with a syringe or Teflon homogenizer, and the protein concentration determined. The membranes are diluted to a protein concentration of 1–5 mg/ml in Hepes buffer, aliquoted and kept at −80° C. until use.

Aliquots of the membrane suspension are incubated for 60 min at 25° C. with 30 pM [$^{125}$I]-iodoproxifan, a known compound with high affinity for the H3 receptor, and the test compound at various concentrations. The incubation is stopped by dilution with ice-cold medium, followed by rapid filtration through Whatman GF/B filters pretreated for 1 hour with 0.5% polyethyleneimine. The radioactivity retained on the filters is counted using a Cobra II auto gamma counter. The radioactivity of the filters is indirectly proportional to the binding affinity of the tested compound. The results are analysed by nonlinear regression analysis.

When tested, the present compounds of the formula (I) generally show a high binding affinity to the histamine H3 receptor.

Functional Assay I

The ability of the compounds to interact with the histamine H3 receptor as agonists, inverse agonists and/or antagonists, is determined by an in vitro functional assay utilizing membranes from HEK 293 cell expressing the human H3 receptors.

The H3 receptor is cloned by PCR and subcloned into the pcDNA3 expression vector. Cells stably expressing the H3 receptor are generated by transfecting the H3-expression vectors into HEK 293 cells and using G418 to select for H3 clones. The human H3-HEK 293 clones are cultured in DMEM with glutamax, 10% foetal calf serum, 1% penicillin/streptavidin and 1 mg/ml G418 at 37° C. and 5% CO$_2$.

The H3 receptor expressing cells are washed once with phosphate buffered saline (PBS) and harvested using versene (GIBCO-BRL). PBS is added and the cells are centrifuged for 5 min at 364 g. The cell pellet is resuspended in stimulation buffer to a concentration of 1×10$^6$ cells/ml. cAMP accumulation is measured using the Flash Plate® cAMP assay (NEN™ Life Science Products). The assay is generally performed as described by the manufacturer. Briefly, 50 μl cell suspension is added to each well of the Flashplate which also contained 25 μl 40 μM isoprenaline, to stimulate cAMP generation, and 25 μl of test compound (either agonists or inverse agonists alone, or agonist and antagonist in combination). The assay can be run in "agonist-mode" which means that the test compound is added, in increasing concentration, on its own, to the cells, and cAMP is measured. If cAMP goes up, it is an inverse agonist; if cAMP does not change, it is a neutral antagonist, and if cAMP goes down, it is an agonist. The assay can also be run in the "antagonist-mode" which means that a test compound is added, in increasing concentrations, together with increasing concentrations of a known H3 agonist (eg RAMHA). If the compound is an antagonist, increasing concentrations of it cause a right-ward shift in the H3 agonist's dose-response curves. The final volume in each well is 100 µl. Test compounds are dissolved in DMSO and diluted in $H_2O$. The mixture is shaken for 5 min, and allowed to stand for 25 min at room temperature. The reaction is stopped with 100 µl "Detection Mix" per well. The plates are then sealed with plastic, shaken for 30 min, allowed to stand overnight, and finally the radioactivity is counted in the Cobra II auto gamma topcounter. $EC_{50}$ values are calculated by non-linear regression analysis of dose response curves (6 points minimum) using GraphPad Prism. Kb values are calculated by Schild plot analysis.

Functional Assay II

The ability of the compounds to bind and interact with the human, monkey or rat H3 receptor as agonists, inverse agonists and/or antagonists, is determined by a functional assay, named [$^{35}$S] GTPγS assay.

The human H3 receptor has the following sequence:

Met-Glu-Arg-Ala-Pro-Pro-Asp-Gly-Pro-Leu-Asn-Ala-
Ser-Gly-Ala-Leu-Ala-Gly-Glu-Ala-Ala-Ala-Ala-Gly-
Gly-Ala-Arg-Gly-Phe-Ser-Ala-Ala-Trp-Thr-Ala-Val-
Leu-Ala-Ala-Leu-Met-Ala-Leu-Leu-Ile-Val-Ala-Thr-
Val-Leu-Gly-Asn-Ala-Leu-Val-Met-Leu-Ala-Phe-Val-
Ala-Asp-Ser-Ser-Leu-Arg-Thr-Gln-Asn-Asn-Phe-Phe-
Leu-Leu-Asn-Leu-Ala-Ile-Ser-Asp-Phe-Leu-Val-Gly-
Ala-Phe-Cys-Ile-Pro-Leu-Tyr-Val-Pro-Tyr-Val-Leu-
Thr-Gly-Arg-Trp-Thr-Phe-Gly-Arg-Gly-Leu-Cys-Lys-
Leu-Trp-Leu-Val-Val-Asp-Tyr-Leu-Leu-Cys-Thr-Ser-
Ser-Ala-Phe-Asn-Ile-Val-Leu-Ile-Ser-Tyr-Asp-Arg-
Phe-Leu-Ser-Val-Thr-Arg-Ala-Val-Ser-Tyr-Arg-Ala-
Gln-Gln-Gly-Asp-Thr-Arg-Arg-Ala-Val-Arg-Lys-Met-
Leu-Leu-Val-Trp-Val-Leu-Ala-Phe-Leu-Leu-Tyr-Gly-
Pro-Ala-Ile-Leu-Ser-Trp-Glu-Tyr-Leu-Ser-Gly-Gly-
Ser-Ser-Ile-Pro-Glu-Gly-His-Cys-Tyr-Ala-Glu-Phe-
Phe-Tyr-Asn-Trp-Tyr-Phe-Leu-Ile-Thr-Ala-Ser-Thr-
Leu-Glu-Phe-Phe-Thr-Pro-Phe-Leu-Ser-Val-Thr-Phe-
Phe-Asn-Leu-Ser-Ile-Tyr-Leu-Asn-Ile-Gln-Arg-Arg-
Thr-Arg-Leu-Arg-Leu-Asp-Gly-Ala-Arg-Glu-Ala-Ala-
Gly-Pro-Glu-Pro-Pro-Pro-Glu-Ala-Gln-Pro-Ser-Pro-
Pro-Pro-Pro-Pro-Gly-Cys-Trp-Gly-Cys-Trp-Gln-Lys-
Gly-His-Gly-Glu-Ala-Met-Pro-Leu-His-Arg-Tyr-Gly-

-continued
Val-Gly-Glu-Ala-Ala-Val-Gly-Ala-Glu-Ala-Gly-Glu-
Ala-Thr-Leu-Gly-Gly-Gly-Gly-Gly-Gly-Gly-Ser-Val-
Ala-Ser-Pro-Thr-Ser-Ser-Ser-Gly-Ser-Ser-Ser-Arg-
Gly-Thr-Glu-Arg-Pro-Arg-Ser-Leu-Lys-Arg-Gly-Ser-
Lys-Pro-Ser-Ala-Ser-Ser-Ala-Ser-Leu-Glu-Lys-Arg-
Met-Lys-Met-Val-Ser-Gln-Ser-Phe-Thr-Gln-Arg-Phe-
Arg-Leu-Ser-Arg-Asp-Arg-Lys-Val-Ala-Lys-Ser-Leu-
Ala-Val-Ile-Val-Ser-Ile-Phe-Gly-Leu-Cys-Trp-Ala-
Pro-Tyr-Thr-Leu-Leu-Met-Ile-Ile-Arg-Ala-Ala-Cys-
His-Gly-His-Cys-Val-Pro-Asp-Tyr-Trp-Tyr-Glu-Thr-
Ser-Phe-Trp-Leu-Leu-Trp-Ala-Asn-Ser-Ala-Val-Asn-
Pro-Val-Leu-Tyr-Pro-Leu-Cys-His-His-Ser-Phe-Arg-
Arg-Ala-Phe-Thr-Lys-Leu-Leu-Cys-Pro-Gln-Lys-Leu-
Lys-Ile-Gln-Pro-His-Ser-Ser-Leu-Glu-His-Cys-Trp-
Lys The monkey H3 receptor has the following sequence:

Met-Glu-Arg-Ala-Pro-Pro-Asp-Gly-Pro-Leu-Asn-Ala-
Ser-Gly-Ala-Leu-Ala-Gly-Glu-Ala-Ala-Ala-Ala-Gly-
Gly-Ala-Arg-Gly-Phe-Ser-Ala-Ala-Trp-Thr-Ala-Val-
Leu-Ala-Ala-Leu-Met-Ala-Leu-Leu-Ile-Val-Ala-Thr-
Val-Leu-Gly-Asn-Ala-Leu-Val-Met-Leu-Ala-Phe-Val-
Ala-Asp-Ser-Ser-Leu-Arg-Thr-Gln-Asn-Asn-Phe-Phe-
Leu-Leu-Asn-Leu-Ala-Ile-Ser-Asp-Phe-Leu-Val-Gly-
Ala-Phe-Cys-Ile-Pro-Leu-Tyr-Val-Pro-Tyr-Val-Leu-
Thr-Gly-Arg-Trp-Thr-Phe-Gly-Arg-Gly-Leu-Cys-Lys-
Leu-Trp-Leu-Val-Val-Asp-Tyr-Leu-Leu-Cys-Thr-Ser-
Ser-Ala-Phe-Asn-Ile-Val-Leu-Ile-Ser-Tyr-Asp-Arg-
Phe-Leu-Ser-Val-Thr-Arg-Ala-Val-Ser-Tyr-Arg-Ala-
Gln-Gln-Gly-Asn-Thr-Arg-Arg-Ala-Val-Arg-Lys-Met-
Leu-Leu-Val-Trp-Val-Leu-Ala-Phe-Leu-Leu-Tyr-Gly-
Pro-Ala-Ile-Leu-Ser-Trp-Glu-Tyr-Leu-Ser-Gly-Gly-
Ser-Ser-Ile-Pro-Glu-Gly-His-Cys-Tyr-Ala-Glu-Phe-
Phe-Tyr-Asn-Trp-Tyr-Phe-Leu-Ile-Thr-Ala-Ser-Thr-
Leu-Glu-Phe-Phe-Thr-Pro-Phe-Leu-Ser-Val-Thr-Phe-
Phe-Asn-Leu-Ser-Ile-Tyr-Leu-Asn-Ile-Gln-Arg-Arg-
Thr-Arg-Leu-Arg-Leu-Asp-Gly-Ala-Arg-Glu-Ala-Gly-
Gly-Pro-Glu-Pro-Pro-Pro-Glu-Ala-Gln-Pro-Ser-Pro-
Pro-Pro-Pro-Gly-Cys-Trp-Gly-Cys-Trp-Gln-Lys-
Gly-His-Gly-Glu-Ala-Met-Pro-Leu-His-Arg-Tyr-Gly-

-continued
Val-Gly-Glu-Ala-Ala-Ala-Gly-Ala-Glu-Ala-Gly-Glu-

Thr-Ala-Leu-Gly-Gly-Gly-Gly-Gly-Gly-Ser-Ala-

Ala-Ser-Pro-Thr-Ser-Ser-Ser-Gly-Ser-Ser-Ser-Arg-

Gly-Thr-Glu-Arg-Pro-Arg-Ser-Leu-Lys-Arg-Gly-Ser-

Lys-Pro-Ser-Ala-Ser-Ser-Ala-Ser-Leu-Glu-Lys-Arg-

Met-Lys-Met-Val-Ser-Gln-Ser-Phe-Thr-Gln-Arg-Phe-

Arg-Leu-Ser-Arg-Asp-Arg-Lys-Val-Ala-Lys-Ser-Leu-

Ala-Val-Ile-Val-Ser-Ile-Phe-Gly-Leu-Cys-Trp-Ala-

Pro-Tyr-Thr-Leu-Leu-Met-Ile-Ile-Arg-Ala-Ala-Cys-

His-Gly-His-Cys-Val-Pro-Asp-Tyr-Trp-Tyr-Glu-Thr-

Ser-Phe-Trp-Leu-Leu-Trp-Ala-Asn-Ser-Ala-Val-Asn-

Pro-Val-Leu-Tyr-Pro-Leu-Cys-His-His-Ser-Phe-Arg-

Arg-Ala-Phe-Thr-Lys-Leu-Leu-Cys-Pro-Gln-Lys-Leu-

Lys-Ile-Gln-Pro-His-Ser-Ser-Leu-Glu-Gln-Cys-Trp-

Lys

The rat H3 receptor has the following sequence:

Met-Glu-Arg-Ala-Pro-Pro-Asp-Gly-Leu-Met-Asn-Ala-

Ser-Gly-Thr-Leu-Ala-Gly-Glu-Ala-Ala-Ala-Ala-Gly-

Gly-Ala-Arg-Gly-Phe-Ser-Ala-Ala-Trp-Thr-Ala-Val-

Leu-Ala-Ala-Leu-Met-Ala-Leu-Leu-Ile-Val-Ala-Thr-

Val-Leu-Gly-Asn-Ala-Leu-Val-Met-Leu-Ala-Phe-Val-

Ala-Asp-Ser-Ser-Leu-Arg-Thr-Gln-Asn-Asn-Phe-Phe-

Leu-Leu-Asn-Leu-Ala-Ile-Ser-Asp-Phe-Leu-Val-Gly-

Ala-Phe-Cys-Ile-Pro-Leu-Tyr-Val-Pro-Tyr-Val-Leu-

Thr-Gly-Arg-Trp-Thr-Phe-Gly-Arg-Gly-Leu-Cys-Lys-

Leu-Trp-Leu-Val-Val-Asp-Tyr-Leu-Leu-Cys-Ala-Ser-

Ser-Val-Phe-Asn-Ile-Val-Leu-Ile-Ser-Tyr-Asp-Arg-

Phe-Leu-Ser-Val-Thr-Arg-Ala-Val-Ser-Tyr-Arg-Ala-

Gln-Gln-Gly-Asp-Thr-Arg-Arg-Ala-Val-Arg-Lys-Met-

Ala-Leu-Val-Trp-Val-Leu-Ala-Phe-Leu-Leu-Tyr-Gly-

Pro-Ala-Ile-Leu-Ser-Trp-Glu-Tyr-Leu-Ser-Gly-Gly-

Ser-Ser-Ile-Pro-Glu-Gly-His-Cys-Tyr-Ala-Glu-Phe-

Phe-Tyr-Asn-Trp-Tyr-Phe-Leu-Ile-Thr-Ala-Ser-Thr-

Leu-Glu-Phe-Phe-Thr-Pro-Phe-Leu-Ser-Val-Thr-Phe-

Phe-Asn-Leu-Ser-Ile-Tyr-Leu-Asn-Ile-Gln-Arg-Arg-

Thr-Arg-Leu-Arg-Leu-Asp-Gly-Gly-Arg-Glu-Ala-Gly-

Pro-Glu-Pro-Pro-Pro-Asp-Ala-Gln-Pro-Ser-Pro-Pro-

Pro-Ala-Pro-Pro-Ser-Cys-Trp-Gly-Cys-Trp-Pro-Lys-

Gly-His-Gly-Glu-Ala-Met-Pro-Leu-His-Arg-Tyr-Gly-

-continued
Val-Gly-Glu-Ala-Gly-Pro-Gly-Val-Glu-Ala-Gly-Glu-

Ala-Ala-Leu-Gly-Gly-Gly-Ser-Gly-Gly-Gly-Ala-Ala-

Ala-Ser-Pro-Thr-Ser-Ser-Ser-Gly-Ser-Ser-Ser-Arg-

Gly-Thr-Glu-Arg-Pro-Arg-Ser-Leu-Lys-Arg-Gly-Ser-

Lys-Pro-Ser-Ala-Ser-Ser-Ala-Ser-Leu-Glu-Lys-Arg-

Met-Lys-Met-Val-Ser-Gln-Ser-Ile-Thr-Gln-Arg-Phe-

Arg-Leu-Ser-Arg-Asp-Lys-Lys-Val-Ala-Lys-Ser-Leu-

Ala-Ile-Ile-Val-Ser-Ile-Phe-Gly-Leu-Cys-Trp-Ala-

Pro-Tyr-Thr-Leu-Leu-Met-Ile-Ile-Arg-Ala-Ala-Cys-

His-Gly-Arg-Cys-Ile-Pro-Asp-Tyr-Trp-Tyr-Glu-Thr-

Ser-Phe-Trp-Leu-Leu-Trp-Ala-Asn-Ser-Ala-Val-Asn-

Pro-Val-Leu-Tyr-Pro-Leu-Cys-His-Tyr-Ser-Phe-Arg-

Arg-Ala-Phe-Thr-Lys-Leu-Leu-Cys-Pro-Gln-Lys-Leu-

Lys-Val-Gln-Pro-His-Gly-Ser-Leu-Glu-Gln-Cys-Trp-

Lys

The assay measures the activation of G proteins by catalyzing the exchange of guanosine 5'-diphosphate (GDP) by guanosine 5'-triphosphate (GTP) at the α-subunit. The GTP-bounded G proteins dissociate into two subunits, $G\alpha_{GTP}$ and $G\beta\gamma$, which in turn regulate intracellular enzymes and ion channels. GTP is rapidly hydrolysed by the Gα-subunit (GTPases) and the G protein is deactivated and ready for a new GTP exchange cycle. To study the function of ligand induced G protein coupled receptor (GPCR) activation by an increase in guanine nucleotide exchange at the G proteins, the binding of [$^{35}$S]-guanosine-5'-O-(3-thio) triphosphate ([$^{35}$S] GTPγS), a non-hydrolysed analogue of GTP, is determined. This process can be monitored in vitro by incubating cell membranes containing the G protein coupled receptor H3 with GDP and [$^{35}$S] GTPγS. Cell membranes are obtained from CHO cells stably expressing the human H3 receptor or from HEK 293 cells stably expressing the rat or monkey H3 receptor. The cells are washed twice in PBS, harvested with PBS+1 mM EDTA, pH 7.4 and centrifuged at 280 g for 5 min. The cell pellet is homogenized in 10 ml ice-cold Hepes buffer (20 mM Hepes, 10 mM EDTA pH 7.4 (NaOH)) using an Ultra-Turrax homogenizer for 30 seconds and centrifuged for 15 min at 30.000 g. Following this centrifugation step, the membrane pellet is resuspended in 10 ml ice-cold Hepes buffer (20 mM Hepes, 0.1 mM EDTA pH 7.4 (NaOH)) and homogenized as describe above. This procedure is repeated twice except for the last homogenization step, the protein concentration is determined and membranes are diluted to a protein concentration of 2 mg/ml, aliquoted and kept at −80° C. until use.

In order to study the presence and the potency of an inverse agonist/antagonist the H3-receptor agonist ligand R-α-methyl histamine (RAMHA) is added. The ability of the test compound to counteract the effect of RAMHA is measured. When studying the effect of an agonist RAMHA is not added to the assay medium. The test compound is diluted in the assay buffer (20 mM HEPES, 120 mM NaCl, 10 mM MgCl$_2$ pH 7.4 (NaOH)) at various concentrations followed by addition of 10$^{-8}$ nM RAMHA (only in the case where an inverse agonist/antagonist is examined), 3 μM GDP, 2.5 μg membranes, 0.5 mg SPA beads and 0.1 nM [$^{35}$S] GTPγS and incubated for 2 hours by slightly shaking at room temperature. For the rat and monkey H3 receptor 10 μg membranes including 10 μg/ml saponin are used. The plates are centrifuged at 420 g for 10 min and the radioactivity is measured using a Top-counter. The results are analyzed by non linear regression and the IC$_{50}$ value is determined.

RAMHA and other H3 agonists stimulate the binding of [$^{35}$S] GTPγS to membranes expressing the H3 receptor. In the antagonist/inverse agonist test, the ability of increasing amounts of test compound to inhibit the increased [$^{35}$S] GTPγS binding by 10$^{-5}$ M RAMHA is measured as a decrease in radioactivity signal. The IC$_{50}$ value determined for an antagonist is the ability of this compound to inhibit the effect of 10$^{-8}$ M RAMHA by 50%. In the agonist test, the ability of increasing amounts of test compound is measured as an increase in radioactivity signal. The EC$_{50}$ value determined for an agonist, is the ability of this compound to increase the signal by 50% of the maximal signal that is obtained by 10–5 M RAMHA.

Preferably, the antagonists and agonists according to the invention have an IC$_{50}$/EC$_{50}$ value as determined by one or more of the assays of less than 10 μM, more preferred of less than 1 μM, and even more preferred of less than 500 nM, such as of less than 100 nM.

The Open Cage Schedule-Fed Rat Model

The ability of the present compounds to reduce weight is determined using the in vivo open cage Schedule-fed rat model.

Sprague-Dawley (SD) male rats of an age of about 1½ to 2 months and a weight of about 200–250 g are purchased from Møllegård Breeding and Research Centre A/S (Denmark). On arrival they are allowed some days of acclimatisation before being placed in individual open plastic cages. They are habituated to the presence of food (Altromin pelleted rat chow) in their home cage only during 7 hours in the morning from 07.30 to 14.30 all days a week. Water is present ad libitum. As the consumption of food has stabilised after 7 to 9 days, the animals are ready for use.

Each animal is used only once to avoid carry-over effects between treatments. During the test sessions, the test compound is administered intraperitoneally or orally 30 min before the start of the sessions. One group of animals is administered the test compound at different doses and a control group of animals is given a vehicle. Food and water intake are monitored at 1, 2 and 3 hours post administration.

Any side effects may rapidly be discovered (barrel-rolling, bushy fur etc.) since the animals are kept in transparent plastic cages to enable continuous monitoring.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

Various references are cited herein, the disclosure of which are incorporated by reference in their entireties.

What is claimed is:
1. A compound of the general formula (I):

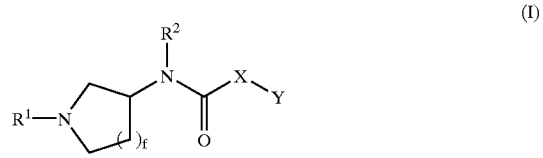

wherein
R$^1$ represents
hydrogen,
C$_{1-8}$-alkyl, C$_{3-8}$-alkenyl or C$_{3-8}$-alkynyl,
which may optionally be substituted with one or more halogen atoms,
cyclobutyl, C$_{3-7}$-cycloalkenyl, C$_{4-8}$-bicycloalkyl, C$_{3-7}$-cycloalkyl-C$_{1-3}$-alkyl or C$_{3-7}$-cycloalkenyl-C$_{1-3}$-alkyl,
which may optionally be substituted at any position with one or more halogen atoms,
R$^2$ represents C$_{1-6}$-alkyl,
f is 0, 1 or 2,
X represents —(CH$_2$)$_m$—(Z)$_n$—(CH$_Z$)$_o$—,
m and o independently are 0, 1, 2, 3 or 4,
n is 0 or 1,
Z is —O—, —NH—, —N(CH$_3$)—, —C(=O)—, —CH(OH)—, —CH(O—C$_{1-6}$-alkyl)-, —C(=N—OH)—, —S—, —S(=O)—, —S=O)$_2$—, —CH=CH— or —C=C—,
Y is
(a) aryl or heteroaryl, which may optionally be substituted with one or more substituents selected from halogen, nitro, cyano, hydroxy, C$_{1-6}$-alkanoyl, C$_{1-6}$-alkylthio, C$_{1-6}$-alkylsulfonyl, C$_{1-6}$-alkyl, C$_{1-6}$-alkoxy, C$_{3-8}$-cycloalkyl, trifluoromethyl, trifluoromethoxy, —NR$^3$R$^4$ and —O(C=O)NR$^3$R$^4$, or wherein two substituents in adjacent positions form a radical —O—(CH$_2$)$_{1-3}$—O—, wherein R$^3$ and R$^4$ independently are hydrogen, C$_{1-6}$-alkyl, C$_{3-8}$-cycloalkyl, C$_{1-6}$-alkanoyl or aryl, or R$^3$ and R$^4$ together with the nitrogen atom to which they are attached form a 4 to 7 membered, saturated or unsaturated azetidinyl, pyrrolidinyl, piperidyl or azepanyl ring,
wherein said heteroaryl is selected from the group consisting of furyl, thienyl, pyrrolyl, oxazolyl, thiazolyl, imidazolyl, isoxazolyl, isothiazolyl, 1,2,3-triazolyl, 1,2,4-triazolyl, pyranyl, pyridyl, pyridazinyl, pyrimidinyl, pyrazinyl, 1,2,3-triazinyl, 1,2,4-triazinyl, 1,3,5-triazinyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, tetrazolyl, thiadiazinyl, indolyl, isoindolyl, benzofuryl, benzothienyl, indazolyl, benzimidazolyl, benzothiazolyl, benzoisothiazolyl, benzoxazolyl, benzisoxazolyl, purinyl, quinazolinyl, quinolizinyl, quinolinyl, isoquinolinyl, quinoxalinyl, napththyridinyl, pteridinyl, carbazolyl, azepinyl, diazepinyl, acridinyl and partially hydrogenated derivatives thereof
aryl, aryloxy, aryl-C$_{1-6}$-alkyl and aryl-C$_{1-6}$-alkoxy, wherein the ring moieties optionally may be substituted with one or more substituents selected from halogen, nitro, cyano, hydroxy, $C_{1-6}$-alkanoyl, $C_{1-6}$-alkylthio, $C_{1-6}$-alkylsulfonyl, $C_{1-6}$-alkyl, $C_{1-6}$-alkoxy, $C_{3-8}$-cycloalkyl, trifluoromethyl, trifluoromethoxy, —$NR^5R^6$ and —O(C=O)$NR^5R^6$, or wherein two substituents in adjacent positions form a radical —O—$(CH_2)_{1-3}$—O—, wherein $R^5$ and $R^6$ independently are hydrogen, $C_{1-6}$-alkyl, $C_{3-8}$-cycloalkyl, $C_{1-6}$-alkanoyl or aryl, or $R^5$ and $R^6$ together with the nitrogen atom to which they are attached form a 4 to 7 membered, saturated or unsaturated azetidinyl, pyrrolidinyl, piperidyl or azepanyl ring, (b) $C_{3-8}$-cycloalkyl or $C_{5-8}$-cycloalkenyl, which may optionally be substituted with one or more substituents selected from $C_{1-6}$-alkyl, $C_{1-6}$-alkoxy, $C_{1-6}$-alkylthio, cyano, trifluoromethyl, trifluoromethoxy and halogen, aryl and aryloxy, wherein the ring moieties optionally may be substituted with one or more substituents selected from halogen, nitro, cyano, hydroxy, $C_{1-6}$-alkanoyl, $C_{1-6}$-alkylthio, $C_{1-6}$-alkylsulfonyl, $C_{1-6}$-alkyl, $C_{1-6}$-alkoxy, $C_{3-8}$-cycloalkyl, trifluoromethyl, trifluoromethoxy, —$NR^7R^8$ and —O(C=O)$NR^7R^8$, or wherein two substituents in adjacent positions form a radical —O—$(CH_2)_{1-3}$—O—, wherein $R^7$ and $R^8$ independently are hydrogen, $C_{1-6}$-alkyl, $C_{3-8}$-cycloalkyl, $C_{1-6}$-alkanoyl or aryl, or $R^7$ and $R^8$ together with the nitrogen atom to which they are attached form a 4 to 7 membered, saturated or unsaturated azetidinyl, pyrrolidinyl, piperidyl or azepanyl ring, as well as any diastereomer or enantiomer or tautomeric form thereof including mixtures of these or a pharmaceutically acceptable salt thereof, with the proviso that, when m, n, and o are 0, $R^1$ must not be ethyl, or methyl, and with the proviso that the compound must not be

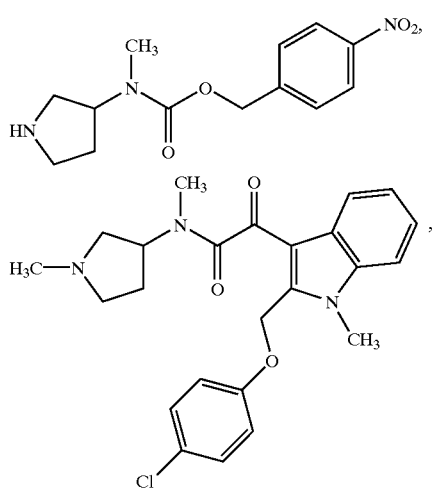

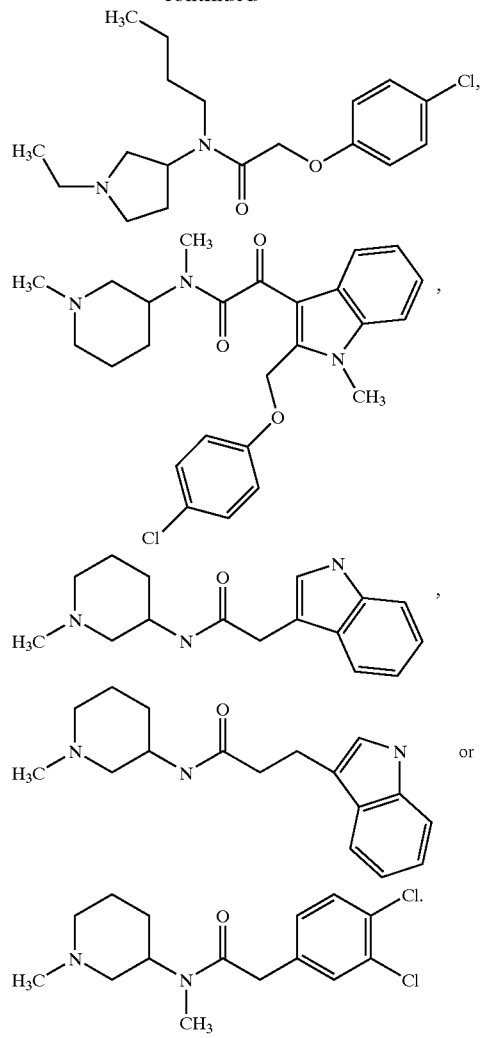

2. A compound according to claim 1, wherein f is 1.

3. A compound according to claim 1, wherein $R^1$ is $C_{1-8}$-alkyl, $C_{3-7}$-cyclo-alkyl-$C_{1-3}$-alkyl or cyclobutyl which may optionally be substituted with one or more halogen atoms.

4. A compound according to claim 3, wherein $R^1$ is $C_{1-8}$-alkyl, $C_{3-7}$-cyclo-alkyl-$C_{1-3}$-alkyl or cyclobutyl.

5. A compound according to claim 4, wherein $R^1$ is $C_{1-8}$-alkyl.

6. A compound according to claim 5, wherein $R^1$ is 1-ethylpropyl.

7. A compound according to claim 5, wherein $R^1$ is 2-propyl.

8. A compound according claim 1, wherein $R^2$ is methyl.

9. A compound according to claim 1, wherein X is —$(CH_2)_m$—C(=O)—$CH_2)_o$—, —$(CH_2)_m$—, a valence bond or —$(CH_2)_m$—CH=CH—$(CH_2)_o$—, wherein m and o are as defined in claim 1.

10. A compound according to claim 9, wherein X is —$(CH_2)_m$—C(=O)—, —$(CH_2)_m$—, a valence bond or —CH=CH—, wherein m is 1, 2, 3 or 4.

11. A compound according to claim 9, wherein X is —$(CH_2)_m$—C(=O)—, —$(CH_2)_m$— or —CH=CH—, wherein m is 1, 2, 3 or 4.

12. A compound according to claim 9, wherein X is —$(CH_2)_2$—C(=O)—, —$CH_2$—, —$(CH_2)_2$—, a valence bond or —CH=CH—.

13. A compound according to claim 9, wherein X is —(CH$_2$)$_2$—C(=O)—, —CH$_2$—, —(CH$_2$)$_2$— or —CH=CH—.

14. A compound according to claim 1, wherein Y is aryl, which may optionally be substituted as defined in claim 1.

15. A compound according to claim 14, wherein Y is phenyl, which may optionally be substituted as defined in claim 1.

16. A compound according to claim 15, wherein Y is phenyl, which may optionally be substituted with one or two of C$_{1-6}$ alkoxy, —NR$^3$R$^4$, halogen, trifluoromethyl or hydroxy, wherein R$^3$ and R$^4$ are as defined in claim 1, two substituents in adjacent positions forming a radical —O—(CH$_2$)$_{1-3}$—O—, or phenyl or phenoxy, which may optionally be substituted as defined in claim 1.

17. A compound according to claim 16, wherein Y is phenyl, which may optionally be substituted with one or two of C$_{1-6}$-alkoxy, —NR$^3$R$^4$, halogen, trifluoromethyl or hydroxy, wherein R$^3$ and R$^4$ independently are hydrogen or C$_{1-6}$-alkyl, a two substituents in adjacent positions forming a radical —O—CH$_2$—O—, or phenyl or phenoxy.

18. A compound according to claim 1 of the general formula (I$_1$);

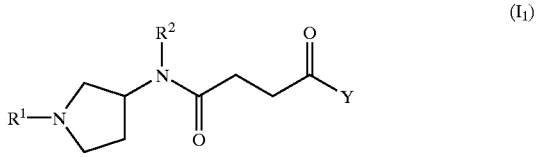

19. A compound according to claim 1 of the general formula (I$_2$);

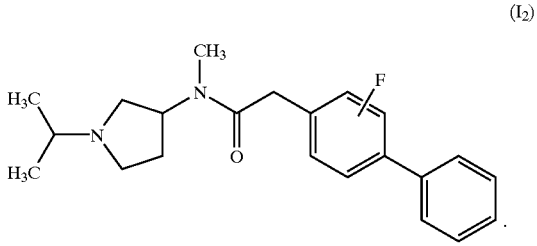

20. A compound according to claim 1 of the general formula (I$_3$):

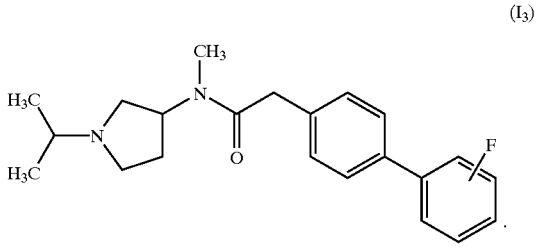

21. A composition comprising, as an active ingredient, the compound of claim 1 together with one or more pharmaceutically acceptable carriers or excipients.

22. A composition according to claim 21 in unit dosage form, comprising from about 0.05 mg to about 1000 mg of said compound.

23. A method for the treatment of disorders or diseases related to the H3 histamine receptor the method comprising administering to a subject in need thereof an effective amount of a compound of the general formula (I'):

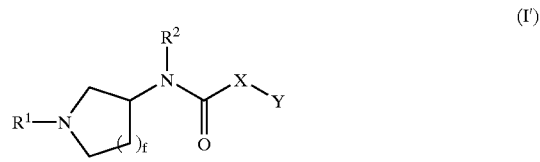

wherein
R$^1$ represents
hydrogen,
C$_{1-8}$-alkyl, C$_{3-8}$-alkenyl or C$_{3-8}$-alkynyl,
which may optionally be substituted with one or more halogen atoms,
C$_{3-7}$-cycloalkyl, C$_{3-7}$-cycloalkenyl, C$_{4-8}$-bicycloalkyl, C$_{3-7}$-cycloalkyl-C$_{1-3}$-alkyl or C$_{3-7}$-cycloalkenyl-C$_{1-3}$-alkyl,
which may optionally be substituted at any position with one or more halogen atoms,
R$^2$ represents C$_{1-6}$-alkyl,
X represents —(CH$_2$)$_m$—(Z)$_n$—(CH$_2$)$_o$—,
m and o independently are 0, 1, 2, 3 or 4,
n is 0 or 1,
Z is —O—, —NH—, —N(CH$_3$)—, —C(=O)—, —CH(OH)—, —C(=N—OH)—, —S—, —S(=O)—, —S(=O)$_2$—, —CH=CH— or —C≡C—,
Y is
(a) aryl or heteroaryl, which may optionally be substituted with one or more substituents selected from
halogen, nitro, cyano, hydroxy, C$_{1-6}$-alkanoyl, C$_{1-6}$-alkylthio, C$_{1-6}$-alkylsulfonyl, C$_{1-6}$-alkyl, C$_{1-6}$-alkoxy, C$_{3-8}$-cycloalkyl, trifluoromethyl, trifluoromethoxy, —NR$^3$R$^4$ and —O(C=O)NR$^3$R$^4$, or wherein two substituents in adjacent positions form a radical —O—(CH$_2$)$_{1-3}$—O—, wherein R$^3$ and R$^4$ independently are hydrogen, C$_{1-6}$-alkyl, C$_{3-8}$-cycloalkyl, C$_{1-6}$-alkanoyl or aryl, or R$^3$ and R$^4$ together with the nitrogen atom to which they are attached form a 4 to 7 membered, saturated or unsaturated azetidinyl, pyrrolidinyl, piperidyl or azepanyl ring,
azyl, aryloxy, aryl-C$_{1-6}$-alkyl and aryl-C$_{1-6}$-alkoxy, wherein the ring moieties optionally may be substituted with one or more substituents selected from
halogen, nitro, cyano, hydroxy, C$_{1-6}$-alkanoyl, C$_{1-6}$-alkylthio, C$_{1-6}$-alkylsulfonyl, C$_{1-6}$-alkyl, C$_{1-6}$-alkoxy, C$_{3-8}$-cycloalkyl, trifluoromethyl, trifluoromethoxy, —NR$^5$R$^6$ and —(C=O)NR$^5$R$^6$, or
wherein two substituents in adjacent positions form a radical —O—(CH$_2$)$_{1-3}$—O—,
wherein R$^5$ and R$^6$ independently are hydrogen, C$_{1-6}$-alkyl, C$_{3-8}$-cycloalkyl, C$_{1-6}$-alkanoyl or aryl, or R$^5$ and R$^6$ together with the nitrogen atom to which they are attached form a 4 to 7 membered, saturated or unsaturated azetidinyl, pyrrolidinyl, piperidyl or azepanyl ring, (b) $C_{3-8}$-cycloalkyl or $C_{5-8}$-cycloalkenyl, which may optionally be substituted with one or more substituents selected from $C_{1-6}$-alkyl, $C_{1-6}$-alkoxy, $C_{1-6}$-alkylthio, cyano, trifluoromethyl, trifluoromethoxy and halogen, aryl and aryloxy, wherein the ring moieties optionally may be substituted with one or more substituents selected from halogen, nitro, cyano, hydroxy, $C_{1-6}$-alkanoyl, $C_{1-6}$-alkylthio, $C_{1-6}$-alkylsulfonyl, $C_{1-6}$-alkyl, $C_{1-6}$-alkoxy, $C_{3-8}$-cycloalkyl, trifluoromethyl, trifluoromethoxy, —$NR^7R^8$ and —O(C=O)$NR^7R^8$, or wherein two substituents in adjacent positions form a radical —O—$(CH_2)_{1-3}$—O—, wherein $R^7$ and $R^8$ independently are hydrogen, $C_{1-6}$-alkyl, $C_{3-8}$-cycloalkyl, $C_{1-6}$-alkanoyl or aryl, or $R^7$ and $R^8$ together with the nitrogen atom to which they are attached form a 4 to 7 membered, saturated or unsaturated azetidinyl, pyrrolidinyl, piperidyl or azepanyl ring, a well as any diastereomer or enantiomer or tautomeric form thereof including mixtures of these or a pharmaceutically acceptable salt thereof for the preparation of a pharmaceutical composition for the treatment of disorders and diseases related to the histamine H3 receptor.

24. The method according to claim 23 wherein the effective amount of the compound is in the range of from about 0.05 mg to about 2000 mg per day.

25. The composition according to claim 21, in unit dosage form, comprising from about 0.1 mg to about 500 mg of said compound.

26. The composition according to claim 21, in unit dosage form, comprising from about 0.5 mg to about 200 mg of said compound.

27. The method according to claim 23, wherein the effective amount of the compound is in the range of from about 0.1 mg to about 1000 mg.

28. The method according to claim 23, wherein the effective amount of the compound is in the range of from about 0.5 mg to about 500 mg.

* * * * *

UNITED STATES PATENT AND TRADEMARK OFFICE
CERTIFICATE OF CORRECTION

PATENT NO. : 6,673,829 B2 Page 1 of 1
APPLICATION NO. : 10/242968
DATED : January 6, 2004
INVENTOR(S) : Dorwald et al.

It is certified that error appears in the above-identified patent and that said Letters Patent is hereby corrected as shown below:

Column 1, line 6:
"filed May 16, 2002" should read--filed May 21, 2002--.

Column 34, line 24, claim 1:
"–$(CH_Z)_o$–" should read --–$(CH_2)_o$–--.

Column 38, line 50, claim 23:
"azyl" should read--aryl--.

Signed and Sealed this

Seventh Day of August, 2007

JON W. DUDAS
*Director of the United States Patent and Trademark Office*